United States Patent
Padula et al.

(10) Patent No.: US 12,357,168 B2
(45) Date of Patent: Jul. 15, 2025

(54) HOLOGRAPHIC REAL SPACE REFRACTIVE SYSTEM

(71) Applicant: NeuroAEye, LLC, Louisville, KY (US)

(72) Inventors: William V. Padula, Killingworth, CT (US); Teddi R. Dinsmore, Killingworth, CT (US)

(73) Assignee: NeuroAeye, LLC, Louisville, KY (US)

( * ) Notice: Subject to any disclaimer, the term of this patent is extended or adjusted under 35 U.S.C. 154(b) by 773 days.

(21) Appl. No.: 17/481,819

(22) Filed: Sep. 22, 2021

(65) Prior Publication Data
US 2022/0007929 A1    Jan. 13, 2022

Related U.S. Application Data

(63) Continuation-in-part of application No. 16/593,619, filed on Oct. 4, 2019, now Pat. No. 11,253,149, which
(Continued)

(51) Int. Cl.
*A61B 3/00* (2006.01)
*A61B 3/024* (2006.01)
(Continued)

(52) U.S. Cl.
CPC ............ *A61B 3/0008* (2013.01); *A61B 3/024* (2013.01); *A61B 3/032* (2013.01); *A61B 3/113* (2013.01); *A61B 5/6803* (2013.01)

(58) Field of Classification Search
CPC ....... A61B 3/0008; A61B 3/024; A61B 3/032; A61B 3/113; A61B 5/6803; A61B 5/0077;
(Continued)

(56) References Cited

U.S. PATENT DOCUMENTS

| 2004/0057013 A1 | 3/2004 | Cappo et al. |
| 2012/0008091 A1 | 1/2012 | Stewart |

(Continued)

FOREIGN PATENT DOCUMENTS

| CN | 107592798 A | 1/2018 |

OTHER PUBLICATIONS

PCT International Search Report and Written Opinion dated Feb. 4, 2022 for PCT Application No. PCT/US2021/051518.
(Continued)

*Primary Examiner* — Tuyen Tra
(74) *Attorney, Agent, or Firm* — GrayRobinson, P.A.

(57) ABSTRACT

A method for testing for visual impairment is provided. The method includes rendering, via a computing device communicatively coupled to a head mounted holographic display device, a virtual target displayed to a user within the holographic display device. The method further includes rendering, via the computing device, at least one virtual light within a field of vision of the user within the holographic display device. The method also includes identifying, via the computing device, whether input was received from the user, wherein the input comprises an indication that the user identified the at least one virtual light. The method further includes generating, via the computing device, a map identifying one or more locations that the user identified the at least one virtual light or did not identify the at least one virtual light.

5 Claims, 27 Drawing Sheets

Related U.S. Application Data is a continuation-in-part of application No. 15/904,995, filed on Feb. 26, 2018, now Pat. No. 10,441,161.

(60) Provisional application No. 63/083,682, filed on Sep. 25, 2020.

(51) Int. Cl.
| | | |
|---|---|---|
| *A61B 3/032* | (2006.01) | |
| *A61B 3/113* | (2006.01) | |
| *A61B 5/00* | (2006.01) | |

(58) Field of Classification Search
CPC .......... A61B 5/745; A61B 3/08; A61B 3/103; A61B 3/028; G02B 2027/014; G02B 2027/0187; G02B 2027/0198; G02B 27/017
USPC .......................................... 351/200, 205, 221
See application file for complete search history.

(56) References Cited

U.S. PATENT DOCUMENTS

| | | |
|---|---|---|
| 2017/0000326 A1 | 1/2017 | Samec et al. |
| 2017/0340200 A1 | 11/2017 | Blaha et al. |
| 2018/0190011 A1 | 7/2018 | Platt et al. |
| 2019/0261847 A1 | 8/2019 | Padula et al. |

OTHER PUBLICATIONS

U.S. Appl. No. 16/593,619, filed Oct. 4, 2019, US 2020/0113434 A1.
Extended European Search Report dated Oct. 19, 2021 for Application No. 19757833.9.
U.S. Appl. No. 15/904,995, filed Feb. 26, 2018, now U.S. Pat. No. 10,441,161.
U.S. Appl. No. 63/083,682, filed Sep. 25, 2020, N/A.
PCT/US2021/0515, Sep. 22, 2021, N/A.

HOLOGRAPHIC REAL SPACE REFRACTIVE SYSTEM

CROSS-REFERENCE TO RELATED APPLICATION

This application is a continuation-in-part of and claims priority to U.S. patent application Ser. No. 16/593,619, filed on Oct. 4, 2019, which is a continuation-in-part application of and claims priority to U.S. patent application Ser. No. 15/904,995, filed on Feb. 26, 2018 (now U.S. Pat. No. 10,441,161). This application also claims priority to a U.S. provisional patent application Ser. No. 63/083,682, filed on Sep. 25, 2020. The prior applications are incorporated herein by reference in their entireties.

BACKGROUND

1. Technical Field

Systems and methods for providing a visual examination using holographic projection in real space and time are provided.

2. Background Art

For over one hundred years, doctors have provided eye examinations including refraction by using lenses and prisms to determine the refractive state and binocularity of the patient. Refraction means to bend light. Persons with myopia (nearsightedness), hyperopia (farsightedness) and astigmatism (two different power curves) performed a refraction to correct the refractive state and blurred vision of the patient by using physical lenses and prisms. While in the 19th century the refraction was mostly conducted with a trial frame by holding up individual lenses before each eye to make the image more clear, in the 20th century the phoropter (meaning "many lenses") was developed. This instrument was extended on the arm of a physical stand and the instrument was positioned before the patient's face. The clinician would then turn the dial to move different lenses in front of the person's eyes to find the best subjective refraction to improve distance vision. The instrument was then advanced to include prisms that could be used to disassociate images or change the position of the image enabling the clinician the ability to evaluate muscle ranges and the ability to maintain eye alignment and binocularity. It also permitted assessment of the person's ability to accommodate or focus at a near range. This was all for the purpose of designing glasses to improve eyesight and visual acuity for both distance and near ranges as well as to prescribe prisms to correct for imbalance in eye alignment affecting binocularity.

While the phoropter is an effective instrument and still used today, it limits the peripheral field and cannot assess binocularity in any other meridian other than primary gaze or looking straight ahead. Binocular imbalances can sometimes only be represented with gaze outside of the primary gaze position. Therefore, the instrument has limited value for these purposes and/or lead the clinician to only be able to prescribe lenses and prisms for one position of the eyes. In addition, the large phoropter blocks the peripheral vision producing an abnormal environment and restriction of side vision, which frequently affects the intensity of the attentional visual process and cause the refractive correction to be too strong or imbalanced.

These and other issues and limitations of existing instruments and technologies are addressed and overcome by the systems and methods of the present disclosure.

SUMMARY OF THE INVENTION

Described herein is a system to evaluate the refractive state of the eye and visual process as well as binocularity in the nine cardinal positions of gaze while in real space by using holographic projection for each eye. The refractive state assessment has been designed to enable the eye of the patient to focus on virtual objects in the manner that the refractive imbalance will focus to maintain clear vision. For example, a object is presented with three dimensions. The myopic eye will focus on the near side of the object and see it with clarity. The dimensions and position of the object is then moved to refocus the far or distance side of the object and calibration is determined as to the power of the eye and the power of the lens required to re-focus the eye to best visual acuity at infinity. The same would occur for the hyperopic eye, only the far portion of the three-dimensional object will be in initial focus.

The patient uses hand movements and/or voice command to communicate the subjective measurement of the dioptric power to correct the vision to best visual acuity and, advantageously, these objectives are accomplished through manipulation of the object in real space. More particularly, in an exemplary embodiment of the present disclosure, an eye with astigmatism would be presented a three dimensional object where perpendicular lines would enable the patient to observe that one of the lines is clear and the other blurred. The object will be rotated to determine the axis of the astigmatism and then the opposite or blurred side of the object would be shifted in space virtually to bring it into focus. This sequence of operation will provide the amount of astigmatism measured in this eye and therefore the predicted amount of cylindrical correction needed to bring clarity. If the patient has both myopia or hyperopia and astigmatism, the object would be simultaneously be manipulated to determine myopia or hyperopia while also evaluation the dioptric power of the astigmatism.

Additional features, functions and benefits of the disclosed systems and methods will be apparent from the detailed description which follows, particularly when read in conjunction with the accompanying figures.

BRIEF DESCRIPTION OF DRAWINGS

Illustrative embodiments are shown by way of example in the accompanying drawings and should not be considered as a limitation of the present disclosure.

DETAILED DESCRIPTION

Apparatus, methods, and non-transitory computer readable medium are described for a holographic eye testing device. Example embodiments provide a device for utilizing holographic virtual projection to perform eye testing, diagnosis, and prescriptive remedy.

In some embodiments, the disclosed holographic eye testing device renders on a head mounted device, one or more three dimensional objects within the holographic display device, wherein the rendering corresponds to a virtual level of depth viewable by a user. The holographic display device updates the rendering of the one or more three dimensional objects, wherein the updates include a virtual movement of the one or more three dimensional objects within the virtual level of depth. The holographic display device receives input from a user, wherein the input includes an indication of alignment of the one or more three dimensional objects based on the virtual movement. The indication of alignment includes a relative position between the one or more three dimensional objects. The holographic display device determines a delta between the relative virtual position between the one or more three dimensional objects and an optimal virtual position. The holographic display device generates prescriptive remedy based on the delta.

Figure 1:
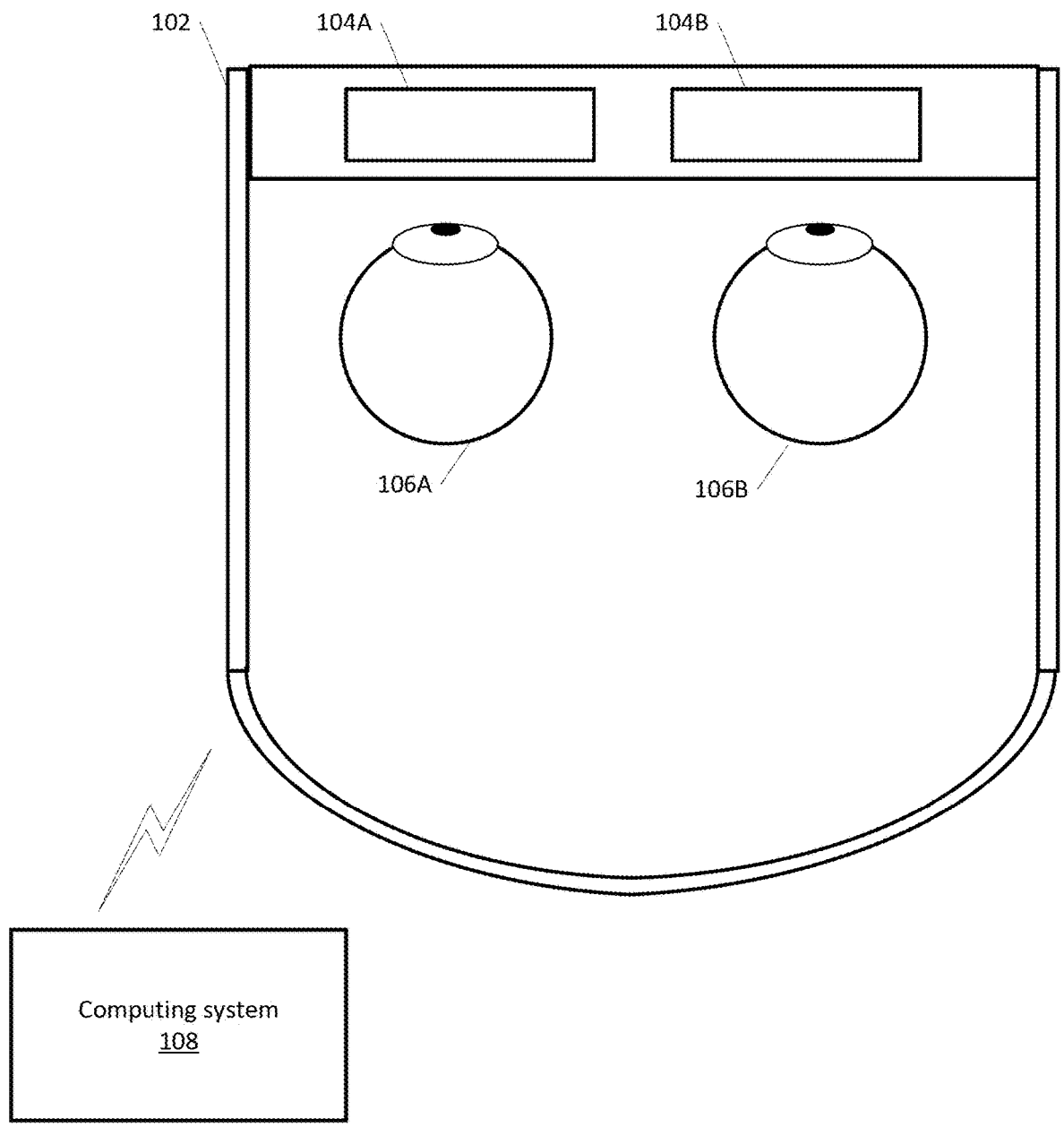
FIG. 1 is a block diagram illustrating a system for the holographic eye testing device according to an exemplary embodiment.

FIG. 1 is a block diagram illustrating a system 100 for the holographic eye testing device according to an exemplary embodiment. In one embodiment, the holographic eye testing device can include a head mounted display (HMD) 102. The HMD 102 can include a pair of combiner lenses 104A, 104B for rendering three dimensional (3D) images within a user's field of view (FOV). The combiner lenses 104A, 104B can be calibrated to the interpupillary distance from the user's eyes 106A, 106B. A computing system 108 can be connected to the combiner lenses 104A, 104B. The holographic eye testing device can be repositioned in any of the nine primary gaze positions as needed. These tests are built to run on technical platforms that can project 3D holographic images within a field of view provided by a wired or wireless headset. The HMD 102 can be connected to an adjustable, cushioned inner headband, which can tilt the combiner lenses 104A, 104B up and down, as well as forward and backward. To wear the unit, the user fits the HMD 102 on their head, using an adjustment wheel at the back of the headband to secure it around the crown, supporting and distributing the weight of the unit equally for comfort, before tilting the visor and combiner lenses 104A, 104B towards the front of the eyes.

The computing system 108 can be inclusive to the HMD 102, where the holographic eye testing device is a self contained apparatus. The computing system 108 in the self contained apparatus can include additional power circuitry to provide electrical current to the parts of the computing system 108. Alternatively, the computing system 108 can be external to the HMD 102 and communicatively coupled either through wired or wireless communication channels to the HMD 102. Wired communication channels can include digital video transmission formats including High Definition Multimedia Interface (HDMI), DisplayPort™ (DisplayPort is a trademark of VESA of San Jose CA, U.S.A.), or any other transmission format capable of propagating a video signal from the computing system 108 to the combiner lenses 104A, 104B. Additionally, the HMD 102 can include speakers or headphones for the presentation of instructional audio to the user during the holographic eye tests. In a wireless communication embodiment, the HMD 102 can include a wireless adapter capable of low latency high bandwidth applications, including but not limited to IEEE 802.11ad. The wireless adapter can interface with the computing system 108 for the transmission of low latency video to be displayed upon the combiner lenses 104, 104B.

Additionally the computing system 108 can include software for the manipulation and rendering of 3D objects within a virtual space. The software can include both platform software to support any fundamental functionality of the HMD 102, such as motion tracking, input functionality, and eye tracking. Platform software can be implemented in a virtual reality (VR) framework, augmented reality (AR) framework, or mixed reality (MR) framework. Platform software to support the fundamental functionality can include but are not limited to SteamVR® (SteamVR is a registered trademark of the Valve Corporation, Seattle WA, U.S.A) software development kit (SDK), Oculus® VR SDK (Oculus is a registered trademark of Oculus VR LLC, Irvine CA, U.S.A.), OSVR (Open source VR) (OSVR is a registered trademark of Razer Asia Pacific Pte. Ltd. Singapore) SDK, and Microsoft Windows Mixed Reality Computing Platform. Application software executing on the computing system 108 with the underlying platform software can be a customized rendering engine, or an off-the-shelf 3D rendering framework, such as Unity® Software (Unity Software is a registered trademark of Unity Technologies of San Francisco CA, U.S.A). The rendering framework can provide the basic building blocks of the virtualized environment for the holographic refractive eye test, including 3D objects and manipulation techniques to change the appearance of the 3D objects. The rendering framework can provide application programming interfaces (APIs) for the instantiation of 3D objects and well-defined interfaces for the manipulation of the 3D objects within the framework. Common software programming language bindings for rendering frameworks include but are not limited to C++, Java, and C#. Additionally, the application software can provide settings to allow a test administrator to adjust actions within the test, such as holographic object speed and object color.

The system 100 can be configured to perform a variety of eyes tests, including, but not limited to, acuity testing (near and far), phorias, horizontal divergence, horizontal convergence, and refraction.

Figure 2:
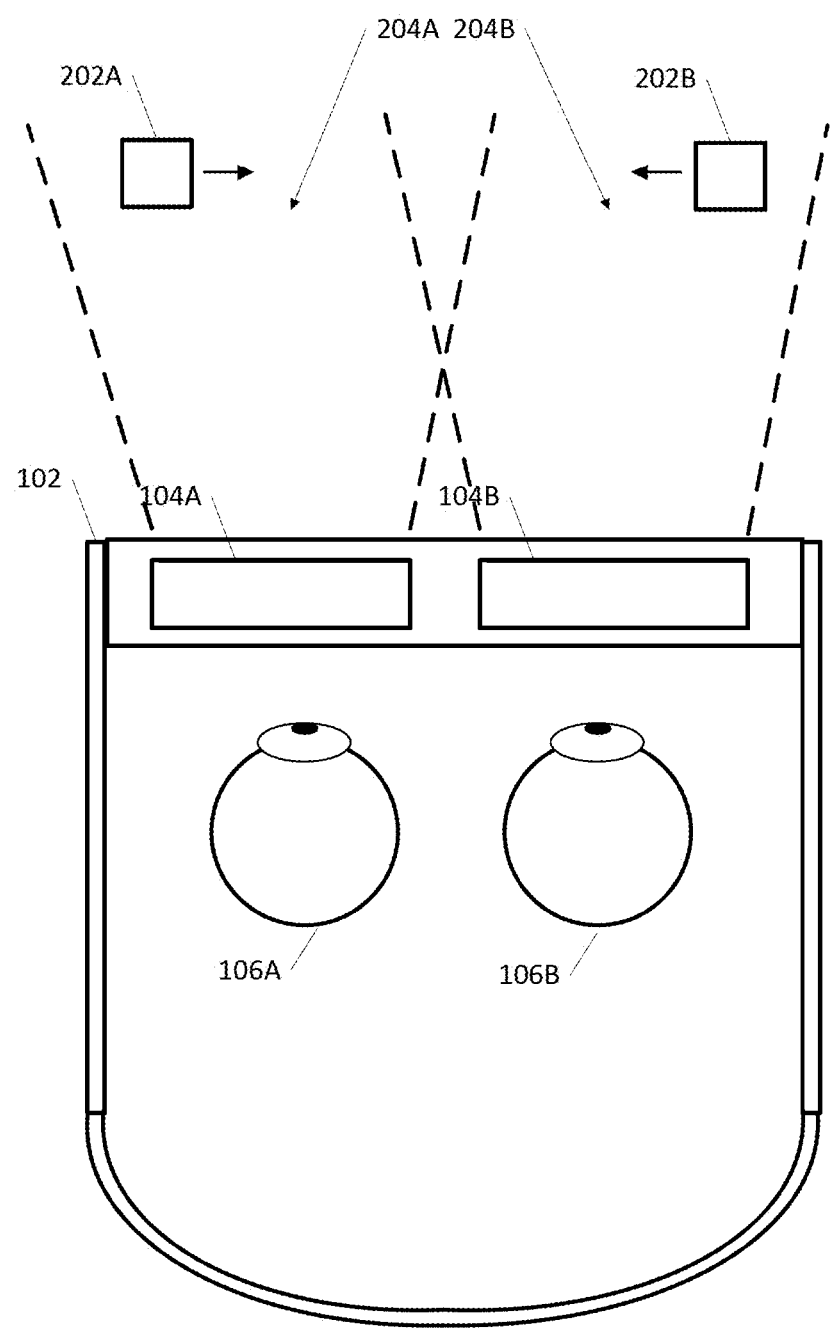
FIG. 2 is a block diagram illustrating a test for horizontal phoria with a holographic eye testing device according to an exemplary embodiment.

FIG. 2 is a block diagram illustrating a test for horizontal phoria with a holographic eye testing device according to an exemplary embodiment. In one embodiment, two virtual 3D objects 202A, 202B can be manipulated in a user's field of view (FOV) 204A, 204B. The virtual 3D objects 202A, 202B can be translated within the same horizontal plane until convergence. The virtual 3D objects 202A, 202B can have a starting point within the user's FOV 204A, 204B equidistant within the same horizontal plane from a mid-point of the FOV. Utilizing application software, the virtual 3D objects 202A, 202B are translated and projected on the combiner lenses 104A, 104B to give the appearance that the virtual 3D objects are a set distance from the view of the user's eyes 106A, 106B. The application software can present the virtual 3D objects 202A, 202B via the combiner lenses 104A, 104B so that the virtual 3D objects can appear to be at different distances from the user's eyes 106A, 106B. In some embodiments, the presentation of the virtual 3D objects 202A, 202B can correspond to projection of the virtual 3D objects at distances of 16 inches to 20 feet in front of the user's eyes 106A, 106B. The range of distances allow phoria to be measured at different intervals of depth for better confidence in convergence results. As the virtual 3D objects 202A, 202B approach the mid-point of the user's FOV, the user can provide input to the application software or platform software. The input can take the form of voice commands, gestures, or input from a "clicker." As the virtual 3D objects 202A, 202B approach each other, they will begin to overlap and converge into a single virtual 3D object. At the point in which the convergence becomes clear to the user, the user can provide input to stop any motion or translation of the virtual 3D objects 202A, 202B. The application software evaluates a delta between the midpoint of the user's FOV 204A, 204B and the point at which the virtual 3D objects 202A, 202B were located when the user provided input to stop the motion or translation. The delta can be represented as a deviation relative to the virtual distance of the virtual 3D objects 202A, 202B from the patient. A diopter is measured by the deviation of the image at a specific virtual distance (1 prism diopter=1 virtual cm deviation of the image at a 1 virtual meter distance).

Figure 3:
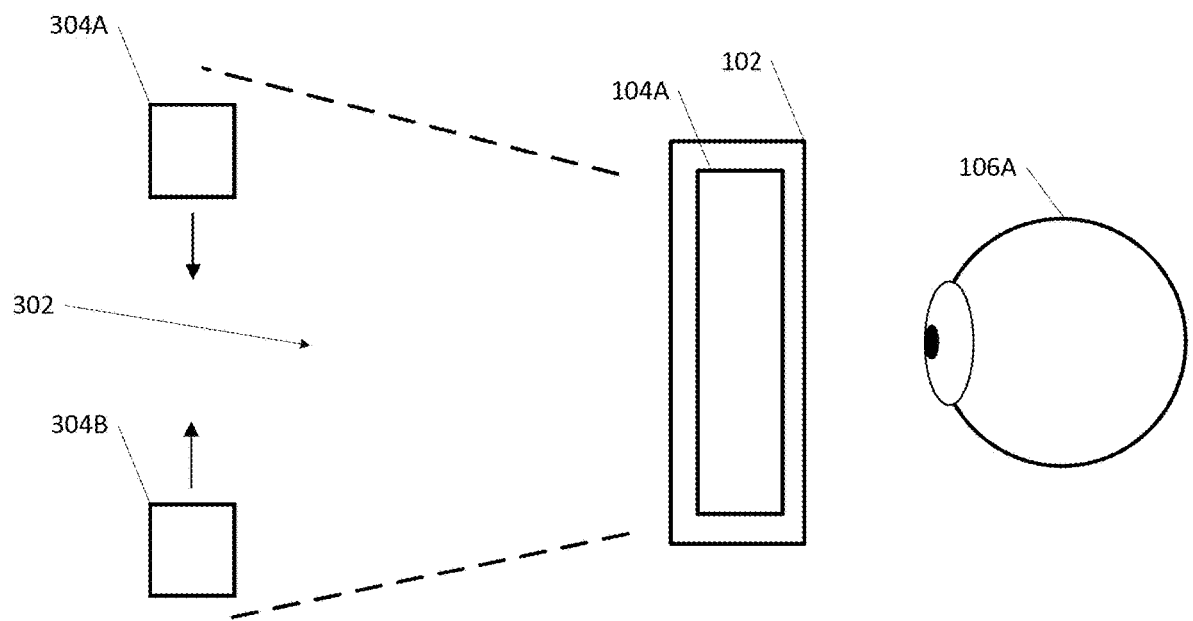
FIG. 3 is a block diagram illustrating a test for vertical phoria utilizing the holographic eye testing device according to an exemplary embodiment.

FIG. 3 is a block diagram illustrating a test for vertical phoria utilizing the holographic eye testing device according to an exemplary embodiment. In one embodiment, two virtual 3D objects 304A, 304B can be manipulated in a user's FOV 302. The virtual 3D objects 304A, 304B can be translated within the same vertical plane until convergence. The virtual 3D objects 304A, 304B can have a starting point within the user's FOV 302 equidistant within the same vertical plane from a mid-point of the FOV. Utilizing application software, the virtual 3D objects 304A, 304B are translated and projected on the combiner lenses 104A, 104B to give the appearance that the virtual 3D objects are a set distance from the view of the user's eyes 106A, 106B. The application software can present the virtual 3D objects 304A, 304B via the combiner lenses 104A, 104B so that the virtual 3D objects can appear to be at different distances from the user's eyes 106A, 106B. In some embodiments, the presentation of the virtual 3D objects 304A, 304B can correspond to projection of the virtual 3D objects at distances of 16 inches to 20 feet in front of the user's eyes 106A, 106B. The range of distances allow phoria to be measured at different intervals of depth for better confidence in convergence results. As the virtual 3D objects 304A, 304B approach the mid-point of the user's FOV 302, the user can provide input to the application software or platform software. The input can take the form of voice commands, gestures, or input from a "clicker." As the virtual 3D objects 304A, 304B approach each other, they will begin to overlap and converge into a single visible virtual 3D object. At the point in which the convergence becomes clear to the user, the user can provide input to stop any motion or translation of the virtual 3D objects 304A, 304B. The application software evaluates a delta between the midpoint of the user's FOV 302 and the point at which the virtual 3D objects 304A, 304B were located when the user provided input to stop the motion or translation. As mentioned above, the delta can be represented as a deviation relative to the virtual distance of the virtual 3D objects 304A, 304B from the patient. A diopter is measured by the deviation of the image at a specific virtual distance (1 prism diopter=1 virtual centimeter deviation of the image at a 1 virtual meter distance).

Figure 4A:
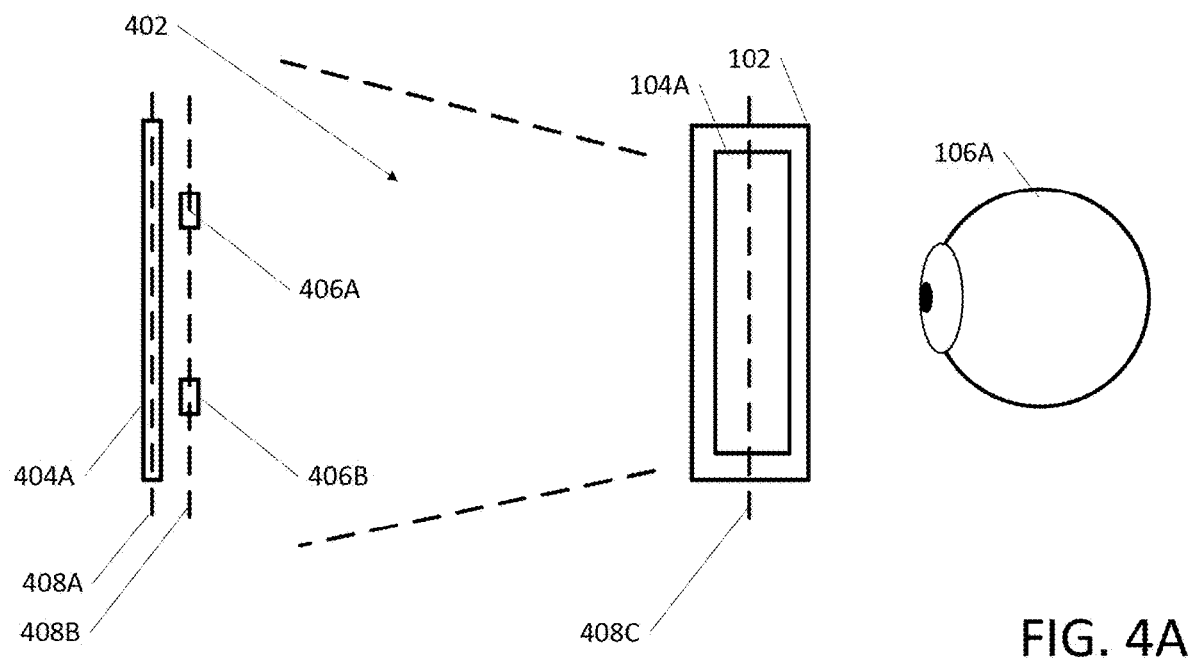
FIG. 4A is a block diagram illustrating a test for astigmatism utilizing the holographic eye testing device according to an exemplary embodiment.

FIG. 4A is a block diagram illustrating a test for astigmatism utilizing the holographic eye testing device according to an exemplary embodiment. In one embodiment, multiple virtual 3D objects 404A, 406A, 406B can be manipulated in a user's FOV 402. The virtual 3D objects 404A, 406A, 406B start in different planes 408A, 408B parallel to the plane of the combiner lenses 408C. In one embodiment, the virtual 3D objects 404A can be a set of vertical lines (relative to the user's eyes 106A, 106B) residing in a plane 408A. Additional virtual 3D objects 406A, 406B can be a set of horizontal lines (relative to the user's eyes 106A, 106B) residing in a plane 408B. When viewed through the combiner lenses 104A, 104B in the FOV 402, the virtual 3D objects 404A, 406A, 406B can appear as a hash mark (#) where the virtual 3D objects appear to intersect, however since they are in different planes 408A, 408B they do not actually intersect.

In one embodiment, the user can start the test by providing input to the computing system 108. The input can take the form of voice commands, including saying key words indicative of beginning the test and/or voice response(s) to automated verbal direction provided by the computing system 108, a hand-held "joy stick", gestures, or providing input from a "clicker." In one embodiment, the user states the word "start" to begin the test. Control of the test can take the form voice commands including "forward" and "backward." A voice command of "forward" translates the plane 408A, and associated virtual 3D objects 404A toward the combiner lenses 104A, 104B. A voice command of "backward" translates the plane 408A, and associated virtual 3D objects 404A away from the combiner lenses 104A, 104B. Utilizing the voice commands and associated translations, a user can manipulated the virtual 3D objects 404A where the user believes the respective planes 408A, 408B and associated virtual 3D objects 404A, 406A, 406B are coincidental. The user can provide a voice command to the computing system 108, such as stating the word "stop" to complete the manipulation portion of the test. Upon the receipt of the "stop" command, the computing system 108 disallows subsequent input commands, such as "forward" and "backward," and determines a delta distance between the final location of the planes 408A, 408B. In the event the user manipulated the planes 408A, 408B to coincide, the delta would be zero.

Figure 4B:
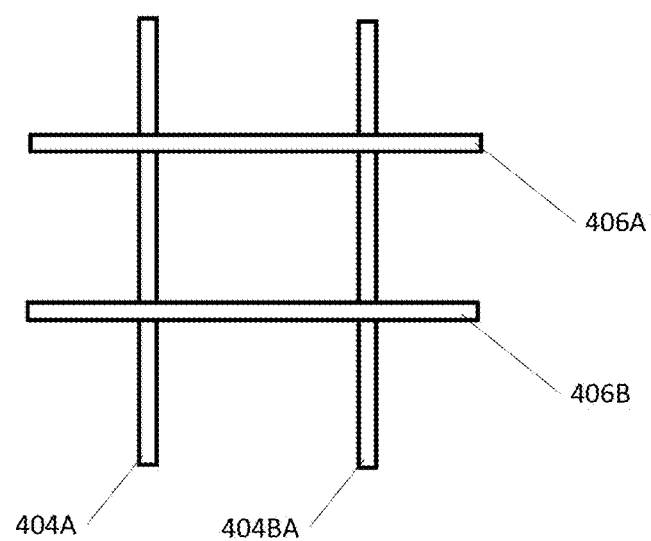
FIG. 4B is a block diagram illustrating a user's perspective of the virtual 3D objects depicted in FIG. 4A according to an exemplary embodiment.

FIG. 4B is a block diagram illustrating a user's perspective of the virtual 3D objects depicted in FIG. 4A. Virtual 3D objects 406A, 406B can be implemented as parallel lines residing the same plane 408B. Virtual 3D objects 404A, 404B can be implemented as parallel lines residing in the same plane 408A.

Figure 5A:
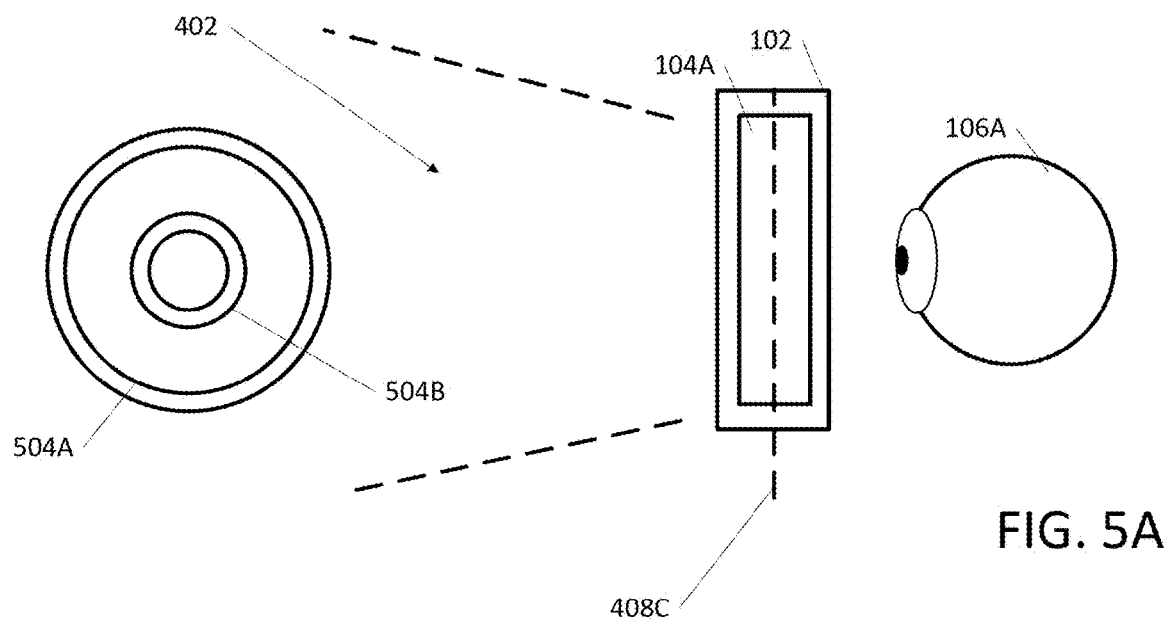
FIG. 5A is a block diagram illustrating a test for astigmatism utilizing the holographic eye testing device according to an exemplary embodiment.
Figure 5B:
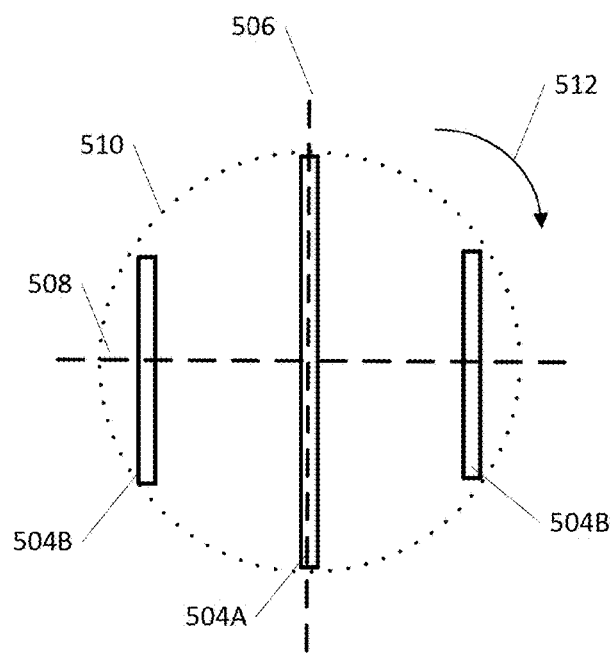
FIG. 5B is a block diagram illustrating a user's perspective of the virtual 3D objects depicted in FIG. 5A according to an exemplary embodiment.

FIG. 5A is a block diagram illustrating a test for astigmatism utilizing the holographic eye testing device according to an exemplary embodiment. FIG. 5B is a block diagram illustrating a user's perspective of the virtual 3D objects depicted in FIG. 5A. In one embodiment, multiple virtual 3D objects 504A, 504B can be manipulated in a user's FOV 402. The virtual 3D objects 504A, 504B correspond to concentric opaque rings across the surface of an invisible sphere 510, where the concentric opaque rings traverse the surface of the sphere perpendicular to the plane of the combiner lenses 104A, 104B. The virtual 3D objects 504A, 504B can be oriented along coaxial planes 506, 508. In other embodiments, the virtual 3D objects 504A, 504B can be distal or proximal portions of concentric opaque rings across the surface of an invisible sphere 510.

In one embodiment, the user can start the test by providing input to the computing system 108. The input can take the form of voice commands, including saying key words indicative of beginning the test, gestures or providing input from a "clicker." The user states the word "start" to begin the test. As the test begins, the invisible sphere 510 and accompanying virtual 3D objects are translated toward the combiner lenses 104A, 104B to give the user the appearance that the virtual 3D objects are coming directly at the user's eyes 106A. When the user can see the virtual 3D objects 504A, 504B clearly, the user can provide input to stop the test in the form of a voice command of "stop." The computing system 108 ceases translation of the invisible sphere 510 and calculates a delta distance from the starting point of the invisible sphere to the point where the invisible sphere resides at the end of the test. A constant point of reference on the invisible sphere 510 can be utilized to determine a consistent location to determine the delta distance.

In another embodiment, the user can start the test by providing input to the computing system 108. The input can take the form of voice commands, including saying key words indicative of beginning the test, gestures or providing input from a "clicker." The user states the word "start" to begin the test. The virtual 3D objects 504A, 504B being the test in a parallel or coincidental plane with a starting plane 506. As the test begins the invisible sphere 510 and accompanying virtual 3D objects are rotated in a clockwise motion 512 from the user's perspective. When the invisible sphere 510 and accompanying virtual 3D objects appear to have rotated ninety (90) degrees from the original starting position, (parallel or coincidental to the horizontal plane 508), the user can provide input to stop the test in the form of a voice command of "stop." The computing system 108 ceases rotation of the invisible sphere 510 and calculates a delta in degrees based on the rotation from the starting point of the invisible sphere to the orientation of the invisible sphere at the end of the test. The delta in degrees can be used to determine the axis of the astigmatism. This provides the amount of astigmatism measured in this eye and therefore the predicted amount of cylindrical correction needed to bring clarity.

Figure 5C:
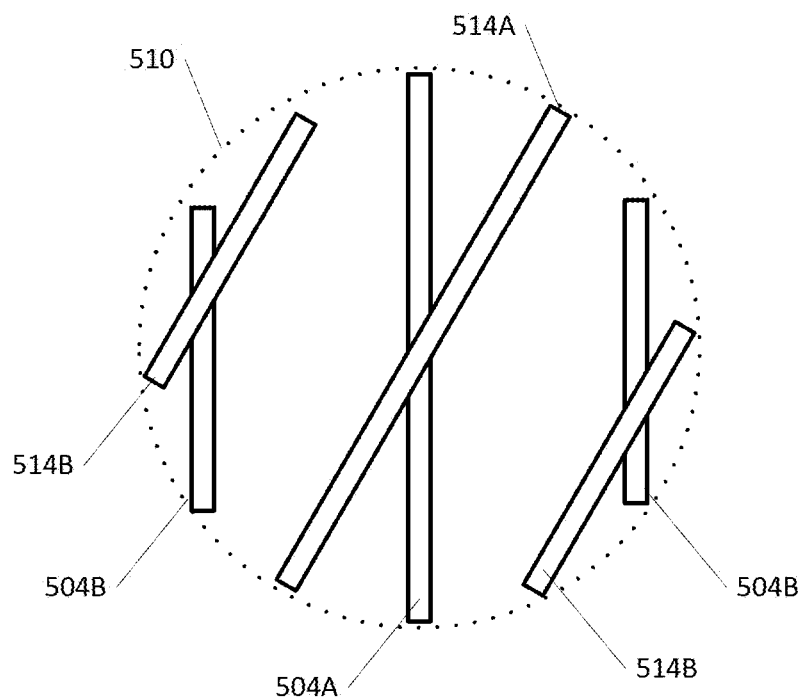
FIG. 5C is a block diagram illustrating another perspective of the virtual 3D objects depicted in FIG. 5A according to an exemplary embodiment.

FIG. 5C is a block diagram illustrating another user's perspective of the virtual 3D objects depicted in FIG. 5A. In another embodiment, the virtual 3D objects 504A, 504B can be distal portions of concentric opaque rings across the surface of an invisible sphere 510. The virtual 3D objects 514A, 514B can be proximal portions of concentric opaque rings across the surface of an invisible sphere 510. The distal portions of the concentric opaque rings form a group and the proximal portions form a group. Groups are rotated and translated in the FOV 402 in unison. The distal portions can be offset from the proximal portions by a rotation of 45 degrees. The user can start the test by providing input to the computing system 108. The input can take the form of voice commands, including saying key words indicative of beginning the test, gestures or providing input from a "clicker." The user states the word "start" to begin the test. The computing system 108 translates virtual 3D objects 514A, 514B corresponding to the proximal portions toward the combiner lenses 104A, 104B where the virtual 3D object 514A, 514B appear to be coming toward the user's eyes 102A, 102B. When the user determines that the virtual 3D objects 514A, 514B are clear and distinct from the distal virtual 3D objects 504A, 504B, the user can provide input to stop the test in the form of a voice command of "stop." The computing system 108 ceases translation of the virtual 3D objects 514A, 514B corresponding to the proximal portions and calculates a delta in distance based on the translation from the starting point to the position at the end of the test.

Figure 6A:
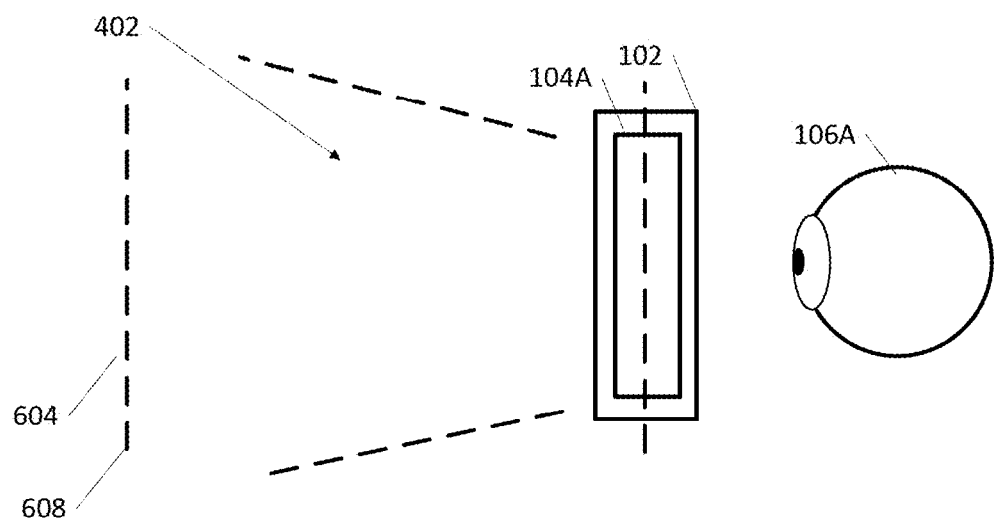
FIGS. 6A-6B are diagrams illustrating a test for visual acuity utilizing the holographic eye testing device according to an exemplary embodiment.

FIG. 6A is a block diagram illustrating a test for visual acuity utilizing the holographic eye testing device, according to an exemplary embodiment. In one embodiment, virtual 2D or 3D letters or images 604 can be displayed and/or manipulated in a user's FOV 402. Utilizing application software, the virtual letters or images 604 are translated and projected on the combiner lenses 104A, 104B to give the appearance that the virtual letters or images 604 are a set distance from the view of the user's eyes 106A, 106B. The application software can present the virtual letters or images 604 via the combiner lenses 104A, 104B so that the virtual letters or images 604 can appear to be at different distances from the user's eyes 106A, 106B. In some embodiments, the presentation of the virtual letters or images 604 can correspond to projection of the virtual letters or images 604 at distances of 16 inches (near visual acuity) to 20 feet (distance visual acuity) in front of the user's eyes 106A, 106B. The visual acuity test is used to determine the smallest letters or images a user can identify from the virtual letters or images 604 at a specified distance away (e.g., 6 meters). The range of distances allows visual acuity to be measured at different intervals of depth.

In one embodiment, the user can start the test by providing input to the computing system 108. The input can take the form of voice commands, including saying key words indicative of beginning the test, gestures or providing input from a "clicker." In one embodiment, the user states the word "start" to begin the test.

In some embodiments, the virtual letters or images 604 can be moved forward or backwards. Control of the test can take the form voice commands including "forward" and "backward." A voice command of "forward" translates the plane 608, and associated virtual letters or images 604 toward the combiner lenses 104A, 104B. A voice command of "backward" translates the plane 608, and associated virtual letters or images 604 away from the combiner lenses 104A, 104B. Utilizing the voice commands and associated translations, a user can manipulated the virtual letters or images 604 until the user can or can no longer identify the virtual letters or images 604. The user can provide a voice command to the computing system 108, such as stating the word "stop" to complete the manipulation portion of the test. Upon the receipt of the "stop" command, the computing system 108 disallows subsequent input commands, such as "forward" and "backward," and determines a final distance of the virtual letters or images 604B.

Figure 6B:
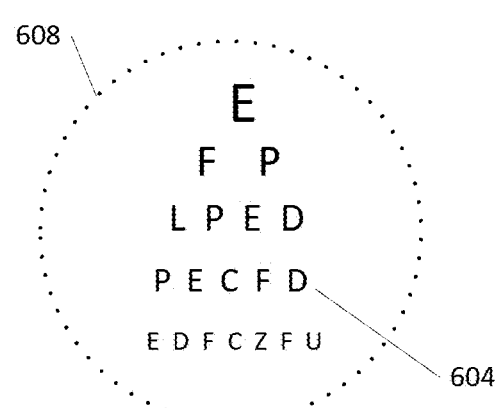

FIG. 6B is a block diagram illustrating a user's perspective of the virtual letters depicted in FIG. 6A. The virtual letters 604 can be implemented as letters residing on the same plane 608. In other embodiments, one or more of the virtual letters 604 can be implemented as letters residing on different planes.

Figure 7A:
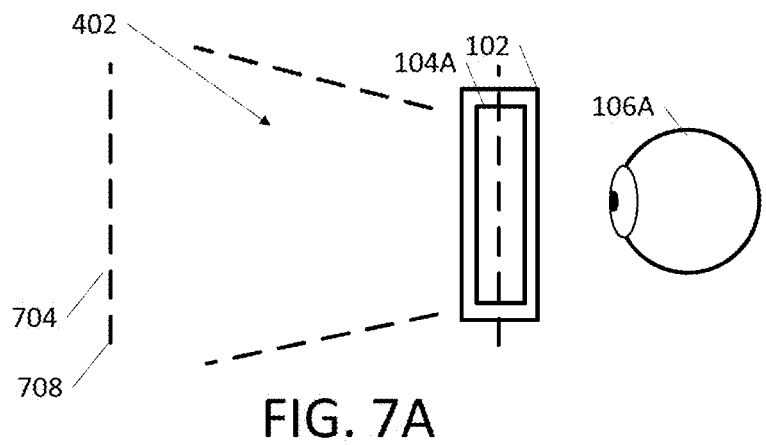
FIGS. 7A-7G are diagrams illustrating tests for horizontal convergent and horizontal divergent, utilizing the holographic eye testing device according to an exemplary embodiment.

FIG. 7A is a block diagram illustrating a test for horizontal convergent and horizontal divergent, utilizing the holographic eye testing device according to an exemplary embodiment. In one embodiment, virtual 2D or 3D shapes 704 can be displayed and/or manipulated in a user's FOV 402. The horizontal convergent and horizontal divergent tests are used to examine eye movement responses to symmetric stimuli.

In one embodiment, the virtual shapes 704 can be manipulated in a user's field of view (FOV) 402. The virtual shapes 704 can have a starting point within the user's FOV 402 equidistant within the same horizontal plane from a midpoint of the FOV 402. Utilizing application software, the virtual shapes 704 are translated and projected on the combiner lenses 104A, 104B to give the appearance that the virtual shapes 704 are a set distance from the view of the user's eyes 106A, 106B. The application software can present the virtual shapes 704 via the combiner lenses 104A, 104B so that the virtual shapes 704 can appear to be at different distances from the user's eyes 106A, 106B. In some embodiments, the presentation of the virtual shapes 704 can correspond to projection of the virtual shapes 704 at distances of 16 inches to 20 feet in front of the user's eyes 106A, 106B. The range of distances allows the horizontal convergent and the horizontal divergent to be measured at different intervals of depth for better confidence in convergence and divergence results.

In one embodiment, the user can start the test by providing input to the computing system 108. The input can take the form of voice commands, including saying key words indicative of beginning the test, gestures or providing input from a "clicker." In one embodiment, the user states the word "start" to begin the test.

Figure 7B:
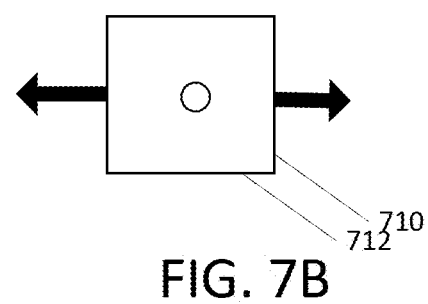
Figure 7C:
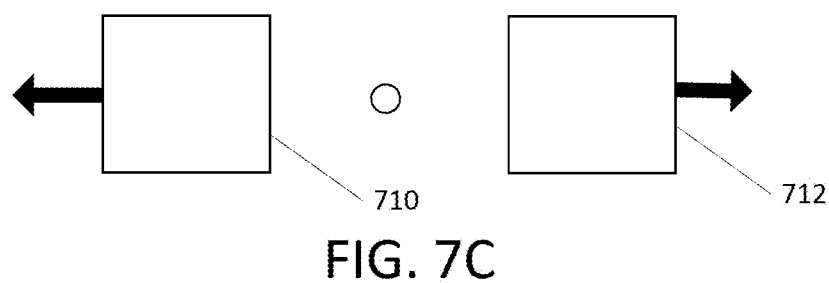

FIGS. 7B-7C are block diagrams illustrating a horizontal convergent test, utilizing the holographic eye testing device according to an exemplary embodiment.

The horizontal convergent test is performed in two stages—a break stage and a recovery stage. Two objects (for example, 3D or 2D shapes, such as 3D cubes) are presented to a user at a given distance. The distance can be changed depending on needs of the user, such as whether the test is being performed for near-sightedness or far-sightedness. A first object 710 of the two objects is projected to a right eye and a second object 712 of the two objects is projected to the left eye.

For the break stage of the test, the first object 710 and the second object 712 begin overlaid on each other and appear as one object, as shown in FIG. 7B. The first object 710 and the second object 712 slowly move apart. The first object 710 shown to the right eye moves to the left from a center start point, and the second object 712 shown to the left eye moves to the right from the center start point, as shown in FIG. 7C. The user reports when the user notices that instead of viewing the single object, the user now views that there are two objects (the first object 710 and the second object 712).

During the break stage, as the first object 710 and the second object 712 move from the center start point of the user's FOV 402, the user can provide input to the application software or platform software. The input can take the form of voice commands, gestures, or input from a "clicker." As the first object 710 moves to the left from the center start point and the second object 712 moves to the right from the center start point, the objects will begin to diverge and appear as separate objects. At the point in which the divergence becomes clear to the user, the user can provide input to stop any motion or translation of the first object 710 and the second object 712. The application software evaluates a delta between the midpoint of the user's FOV 402 and the point at which the first object 710 and the second object 712 were located when the user provided input to stop the motion or translation. The delta can be represented as a deviation relative to the virtual distance of the first object 710 and the second object 712 from the user. A diopter is measured by the deviation of the object at a specific virtual distance (1 prism diopter=1 virtual cm deviation of the object at a 1 virtual meter distance).

Figure 7D:
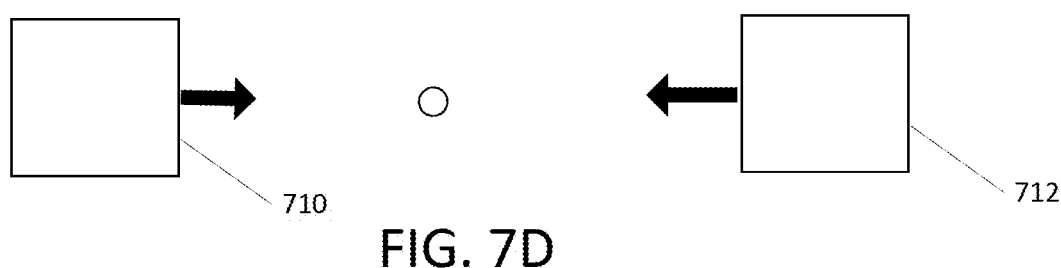

For the recovery stage of the test, the first object 710 and the second object 712 start out offset from each other and slowly move together. The first object 710 shown to the right eye starts on the left side of the user's view and moves to the center start point, and the second object 712 shown to the left eye starts on the right side of the user's view and moves to the center start point, as shown in FIG. 7D. The user reports when the user no longer views two distinct objects, but instead only a single object.

During the recovery stage, as the first object 710 and the second object 712 approach the center start point of the user's FOV 402, the user can provide input to the application software or platform software. The input can take the form of voice commands, gestures, or input from a "clicker." As the first object 710 and the second object 712 approach each other, they will begin to overlap and converge into a single object. At the point in which the convergence becomes clear to the user, the user can provide input to stop any motion or translation of the first object 710 and the second object 712. The application software evaluates a delta between the midpoint of the user's FOV 402 and the point at which the first object 710 and the second object 712 were located when the user provided input to stop the motion or translation. The delta can be represented as a deviation relative to the virtual distance of the first object 710 and the second object 712 from the user. A diopter is measured by the deviation of the object at a specific virtual distance (1 prism diopter=1 virtual cm deviation of the object at a 1 virtual meter distance).

Figure 7E:
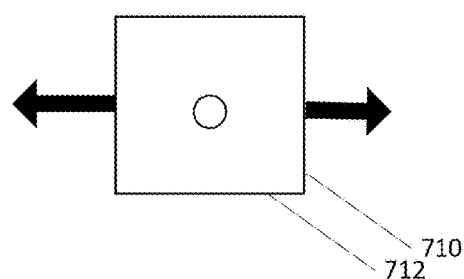
Figure 7F:
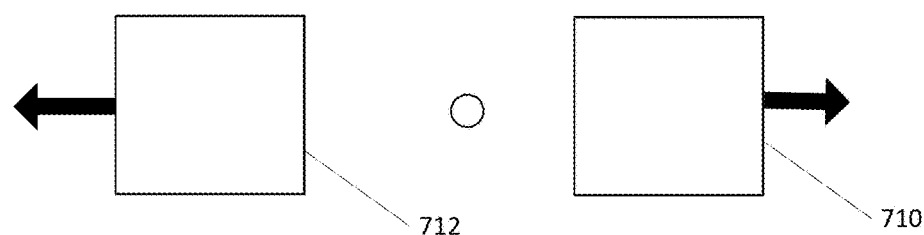
Figure 7G:
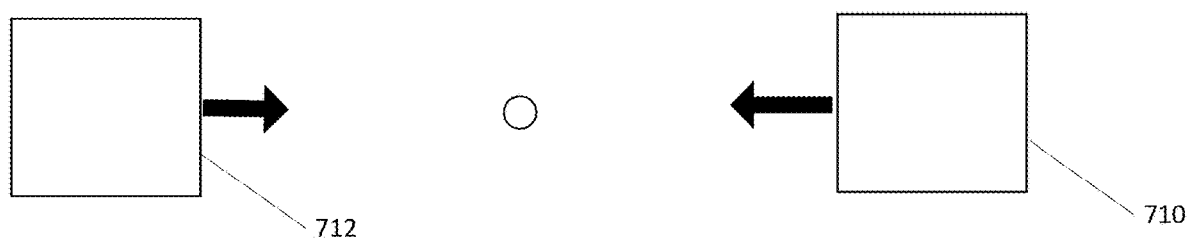

FIGS. 7E-7G is a block diagram illustrating a horizontal divergent test, utilizing the holographic eye testing device according to an exemplary embodiment.

The horizontal divergent is performed in two stages—a break stage and a recovery stage. Two objects (for example, 3D or 2D shapes, such as 3D cubes) are presented to a user at a given distance. The distance can be changed depending on needs of the user, such as whether the test is being performed for near-sightedness or far-sightedness. A first object of the two objects is projected to a right eye and a second object of the two objects is projected to the left eye.

The difference between horizontal divergent test and the horizontal convergent tests has to do with what object is shown to what eye, and where the objects move. For divergent test, the objects are shown to the opposite eye from the convergent test.

For the break stage of the test, the first object 710 and the second object 712 begin overlaid on each other and appear as one object, as shown in FIG. 7E. The first object 710 and the second object 712 slowly move apart. The first object 710 shown to the right eye moves to the right from the center start point, and the second object 712 shown to the left eye moves to the left from the center start point, as shown in FIG. 7F. The user reports when the user notices that instead of viewing the single object, the user now views that there are two objects (the first object 710 and the second object 712).

During the break stage, the first object 710 and the second object 712 move from the center start point of the user's FOV 402, the user can provide input to the application software or platform software. The input can take the form of voice commands, gestures, or input from a "clicker." As the first object 710 moves to the right from the center start point and the second object 712 moves to the left from the center start point, the objects will begin to diverge and appear as separate objects. At the point in which the divergence becomes clear to the user, the user can provide input to stop any motion or translation of the first object 710 and the second object 712. The application software evaluates a delta between the midpoint of the user's FOV 402 and the point at which the first object 710 and the second object 712 were located when the user provided input to stop the motion or translation. The delta can be represented as a deviation relative to the virtual distance of the first object 710 and the second object 712 from the user. A diopter is measured by the deviation of the object at a specific virtual distance (1 prism diopter=1 virtual cm deviation of the object at a 1 virtual meter distance).

For the recovery stage of the test, the first object 710 and the second object 712 start out offset from each other and slowly move together, as shown in FIG. 7G. The first object 710 shown to the right eye starts on the right side of the user's view and moves to the center start point, and the second object 712 shown to the left eye start's on the left side of the user's view and moves to the center start point. The user reports when the user no longer views two distinct objects, but instead only a single object.

During the recovery stage, as the first object 710 and the second object 712 approach the center start point of the user's FOV 402, the user can provide input to the application software or platform software. The input can take the form of voice commands, gestures, or input from a "clicker." As the first object 710 and the second object 712 approach each other, the objects will begin to overlap and converge into a single object. At the point in which the convergence becomes clear to the user, the user can provide input to stop any motion or translation of the first object 710 and the second object 712. The application software evaluates a delta between the midpoint of the user's FOV 402 and the point at which the first object 710 and the second object 712 were located when the user provided input to stop the motion or translation. The delta can be represented as a deviation relative to the virtual distance of the first object 710 and the second object 712 from the user. A diopter is measured by the deviation of the object at a specific virtual distance (1 prism diopter=1 virtual cm deviation of the object at a 1 virtual meter distance).

For both the convergent test and the divergent test described above, the first object 710 is only shown the right eye and the second object 712 is only shown to the left eye. This means at the start of the convergent test and/or the divergent test, a user will see two objects, but if the user closes one eye, only one object will be visible to the user (the one object projected for that eye). This is how a fusion effect is achieved, where two objects suddenly appear to be one, at the start of the divergent test and at the end of the convergent test.

In the above convergent test and/or the divergent test, and along with most of the other tests, eye tracking data is important because it allows the system to determine where the user is looking. For these tests, along with others, the program may request that the user look at a certain point in order to start the test, or to confirm that they are looking in the right location and see the shapes before the test is started. For the phorias testing, the system may request that a user attempt to gaze at a certain point while the shapes are in motion in order to ensure that the tests return accurate results. If they look away from the point, or directly at the shapes, the test may pause and wait for them to return their gaze to the requested object before continuing.

Figure 8A:
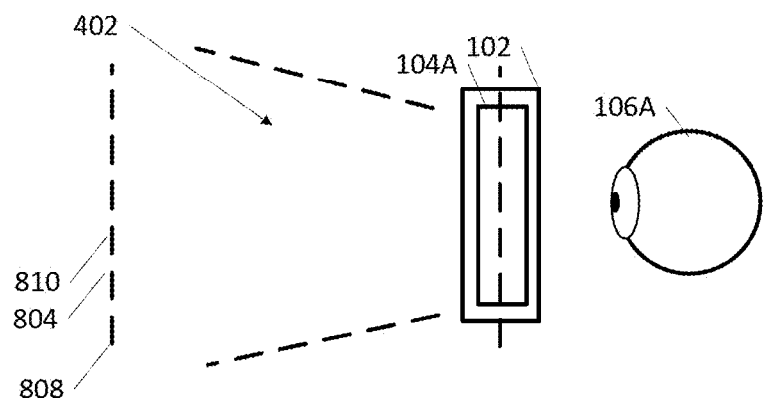
FIGS. 8A-8C are diagrams illustrating refraction testing utilizing the holographic eye testing device according to an exemplary embodiment.
Figure 8B:
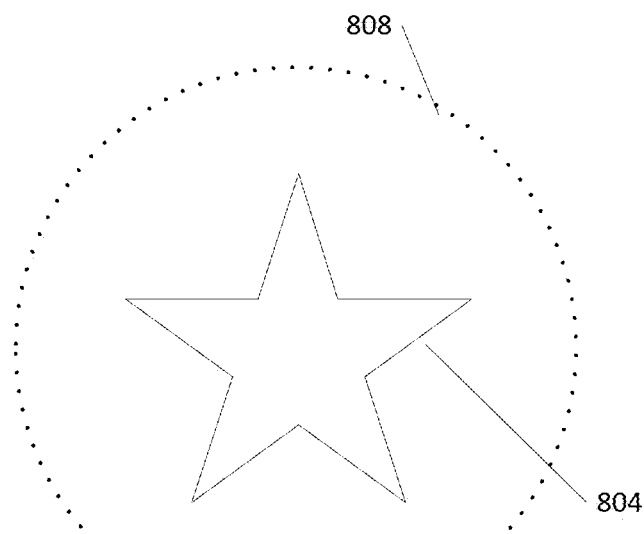
Figure 8C:
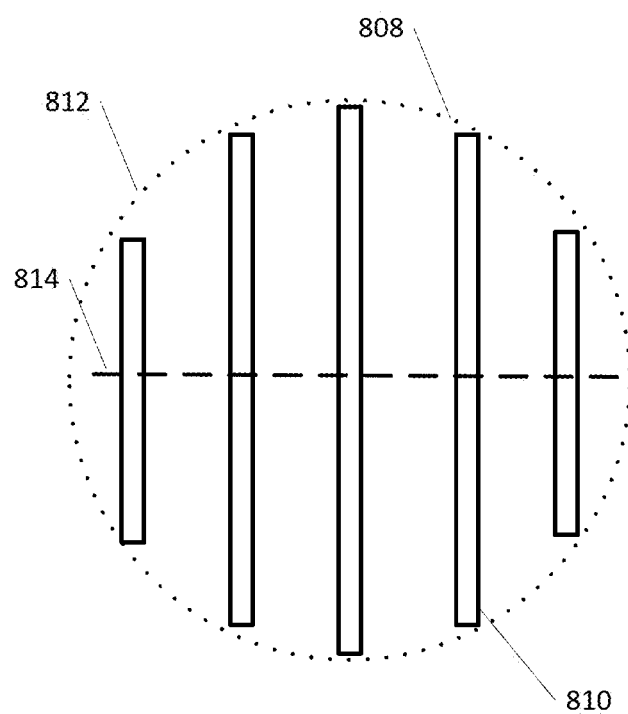

FIGS. 8A-8C are diagrams illustrating refraction testing utilizing the holographic eye testing device according to an exemplary embodiment. As shown in FIG. 8A, in one embodiment, at least one virtual object 804 and/or a series of virtual lines 810 can be displayed and/or manipulated in a user's FOV 402. Utilizing application software, the object 804 or the series of lines 810 are translated on a vertical plane 808 and projected on the combiner lenses 104A, 104B to give the appearance that the object 804 or the series of lines 810 is a set distance from the view of the user's eyes 106A, 106B. The application software can present the object 804 or the series of lines 810 via the combiner lenses 104A, 104B so that the object 804 or the series of lines 810 can appear to be at different distances from the user's eyes 106A, 106B. In some embodiments, the presentation of the object 804 or the series of lines 810 can correspond to projection of virtual letters, images, or lines at distances of 16 inches (near visual acuity) to 20 feet (distance visual acuity) in front of the user's eyes 106A, 106B.

In one embodiment, the user can start the test by providing input to the computing system 108. The input can take the form of voice commands, including saying key words indicative of beginning the test, gestures, or providing input from a "clicker." In one embodiment, the user states the word "start" to begin the test.

The described systems and methods use depth of field for testing refraction. The refraction testing determines the user's level of hyperopia (farsightedness), myopia (nearsightedness), and astigmatism, and three associated numerical values for sphere, cylinder, and axis, typically needed for an eyeglass prescription.

In the first step, the computing system 108 measures the refractive state of the eye by having the user move the object 804 from an initial distance towards or away from the user until a resolution of the object 804 appears clear to the user. The distance at which the object 804 appears clear to the user is labeled as a final distance. The computing system 108 determines an initial measurement between the final position of the virtual object and an optimal virtual position. This initial measurement is at the focal length of the refractive spherical equivalent of the eye and is the sphere power. The sphere power indicates the amount of lens power, measured in diopters (D), prescribed to correct nearsightedness or farsightedness.

In the second step, a series of virtual lines 810 are presented at the final distance in a parallel or coincidental plane with the plane 808. In a first embodiment, the series of lines 810 correspond to concentric opaque rings across the surface of an invisible sphere 812 (shown in FIG. 8C), where the concentric opaque rings traverse the surface of the sphere 812 perpendicular to the plane of the combiner lenses 104A, 104B. In a second embodiment, the series of lines 810 includes a predefined number of lines (for example, three lines) in the axis plane.

In the first embodiment, as the test begins, the invisible sphere 812 and accompanying series of lines 810 are rotated in a clockwise motion from the user's perspective. When the invisible sphere 812 and accompanying series of lines 810 appear to have rotated ninety (90) degrees about an axis from the final position, (parallel or coincidental to the axis 814 shown in FIG. 8C), the user can provide input to stop the test, for example, in the form of a voice command of "stop." The computing system 108 ceases rotation of the invisible sphere 812 and calculates a delta in degrees based on the rotation from the starting point of the invisible sphere 812 to the orientation of the invisible sphere 812 at the end of the test. The delta in degrees can be used to determine the axis value.

The second step provides the axis. This provides the amount of astigmatism measured in this eye and therefore the predicted amount of cylindrical correction needed to bring clarity. The cylinder value refers to the amount of astigmatism in the eyes.

In the third step, the lines 810 are shifted 90 degrees from the axis 814 and moved further away from the user to display a blurred side of the lines 810. The user moves the lines 810 closer to or farther from (plus cylinder or minus cylinder) the user until the lines appear clear to the user. This is the focal length of the cylinder power and corresponds to the difference in power from the sphere.

Based on the above, the sphere, cylinder, and axis values are determined. The above described sequence provides the amount of hyperopia (farsightedness), myopia (nearsightedness), and astigmatism measured in this eye and therefore the predicted amount of correction needed to bring clarity. If the user has both myopia or hyperopia and astigmatism, the object 804 would be simultaneously manipulated to determine myopia or hyperopia while also evaluation the dioptric power of the astigmatism.

In some embodiments, when measuring hyperopia, plus (convex) lenses are included in the HMD 102 underneath the lenses 104A, 104B and in front of the user's eyes 106A, 106B. The reason for this is that the hyperopic eye focuses beyond the fixation object. In order to measure the hyperopia, the hyperopic eye is mathematically made to become myopic An algorithm is used to subtracts the values to determine the dioptric value of the hyperopis.

In some embodiments, a fourth step is included to refine the exact sphere power and then to binocularly balance the prescription for the two eyes. In the fourth step, the object 804 is shifted further away from the user to create +0.50 diopters in each the user's eyes 106A, 106B. The object 804 initially appears as one object to the user and then is disassociated or separated until the user can identify two separate objects. The user reports which object is clearer. The clearer object is then moved away from the user until both objects appear equally as blurred. The objects are then merged and the user moves them closer until the resolution appears best to the user. The binocular balance has then been completed.

The object 804 and lines 810 can be moved forward or backwards or rotated. Control of the test can take the form voice commands including "forward," "backward," and "rotate." A voice command of "forward" translates the plane 808, and associated object 804 or lines 810 toward the combiner lenses 104A, 104B. A voice command of "backward" translates the plane 808, and associated object 804 or lines 810 away from the combiner lenses 104A, 104B. A voice command of "rotate" moves the plane 808, and associated object 804 or lines 810 in a rotation manner Utilizing the voice commands and associated translations, a user can manipulate the object 804 until the user can or can no longer identify the object 804 or lines 810. The user can provide a voice command to the computing system 108, such as stating the word "stop" to complete the manipulation portion of the test.

FIG. 8B is a block diagram illustrating a user's perspective of the virtual object 804 described in FIG. 8A. The virtual object 804 can be implemented as one or more virtual 2D or 3D letters or images, such as shapes, pictures, etc., residing on the plane 808.

FIG. 8C is a block diagram illustrating a user's perspective of the series of lines 810 described in FIG. 8A. The series of lines 810 can be implemented as parallel lines (running vertical and/or horizontal) residing on the plane 808. The series of lines 810 correspond to concentric opaque rings across the surface of the invisible sphere 812, where the concentric opaque rings traverse the surface of the sphere 812 perpendicular to the plane of the combiner lenses 104A, 104B.

Figure 9A:
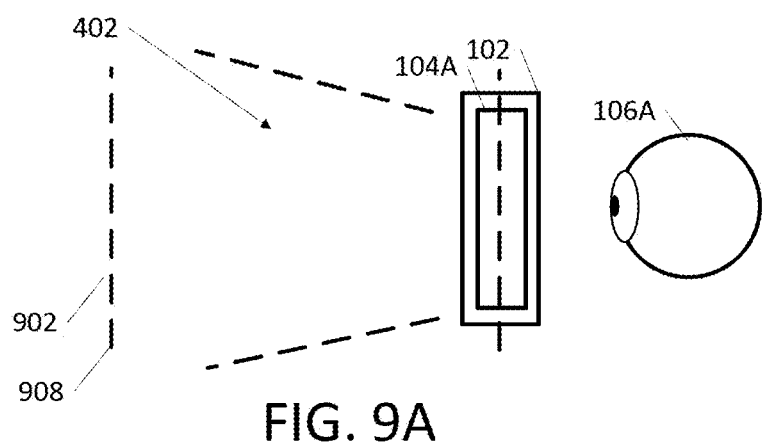
FIGS. 9A-9B are diagrams illustrating convergence testing utilizing the holographic eye testing device according to an exemplary embodiment.

FIG. 9 is a block diagram illustrating convergence testing utilizing the holographic eye testing device according to an exemplary embodiment. The head mounted display (HMD) 102 incorporates eye tracking. Eye tracking enables the HMD 102 to track where the user's eyes 106A, 106B are looking in real time. As shown in FIG. 9A, in one embodiment, at least one virtual object 902 can be displayed and/or manipulated in a user's FOV 402. Utilizing application software, the object 902 is translated on a vertical plane 908 and projected on the combiner lenses 104A, 104B to give the appearance that the object 902 is a set distance from the view of the user's eyes 106A, 106B. The application software can present the object 902 via the combiner lenses 104A, 104B so that the object 902 can appear to be at different distances from the user's eyes 106A, 106B. In some embodiments, the presentation of the object 902 can correspond to projection of virtual letters, images, or lines at distances of 16 inches (near visual acuity) to 20 feet (distance visual acuity) in front of the user's eyes 106A, 106B.

In one embodiment, the user can start the test by providing input to the computing system 108. The input can take the form of voice commands, including saying key words indicative of beginning the test, gestures, or providing input from a "clicker." In one embodiment, the user states the word "start" to begin the test.

During the convergence testing, the object 902 is presented to each eyes 106A, 106B and is moved across the user's FOV 402. The user follows the object 902 from left to right and right to left. The object 902 is then moved in a circle clock wise and counter-clockwise. The HMD 102, via eye tracking, monitors fixation loss and quality of movement of the user's eyes 106A, 106B. Points of fixation loss and the quality of movement are recorded.

Convergence near point will be assessed by rendering a first virtual object 910 displayed to a right eye and a second virtual object 912 displayed to a left eye within the holographic display device, wherein the rendering corresponds to the first virtual object and the second virtual object aligned to appear as one virtual object to the user. The first virtual object 910 and the second virtual object 912 appear at a distance of 40 centimeters in front of the user's eyes 106A, 106B. The user moves the first virtual object 910 and the second virtual object 912 presented to both eyes 106A, 106B toward the user's nose. The HMD 102 monitors eye alignment and record the distance (in centimeter or inches) when the eyes 106A, 106B lose alignment on the first virtual object 910 and the second virtual object 912 and the first virtual object 910 and the second virtual object 912 appears as two separate objects. This is recorded as the break point. The first virtual object 910 and the second virtual object 912 are then moved away from the user and the HMD 102 records the distance when the eyes 106A, 106B realign and the user fuses the first virtual object 910 and the second virtual object 912 back to appear as one virtual object to the user. This is recorded as the realignment point.

Figure 9B:
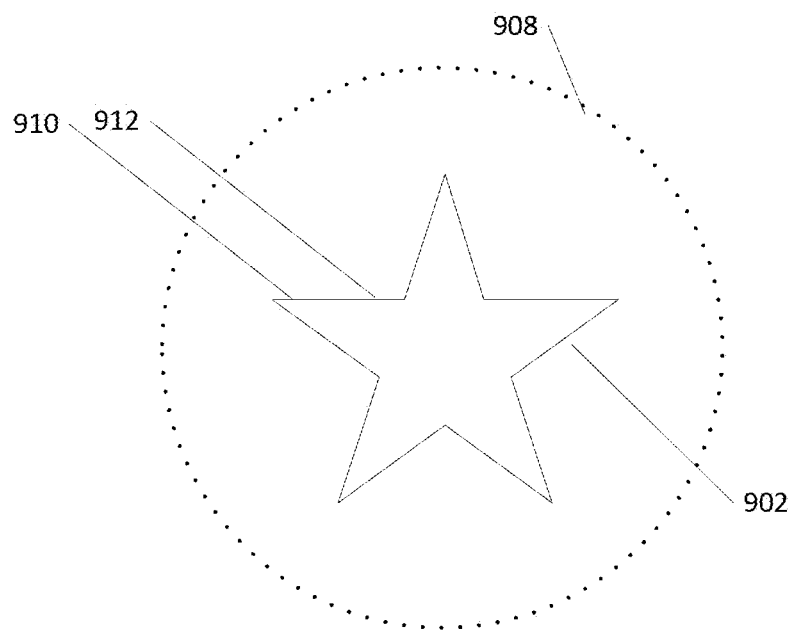

FIG. 9B is a block diagram illustrating a user's perspective of the virtual object 902 and/or the first virtual object 910 and the second virtual object 912 as viewed aligned, as described in FIG. 9A. The virtual object 804 can be implemented as one or more virtual 2D or 3D letters or images, such as shapes, pictures, etc., residing on the plane 908.

FIGS. 10A-10D illustrates methods for diagnosis and/or prescription of remedies for visual impairment in accordance with exemplary embodiments.

Figure 10A:
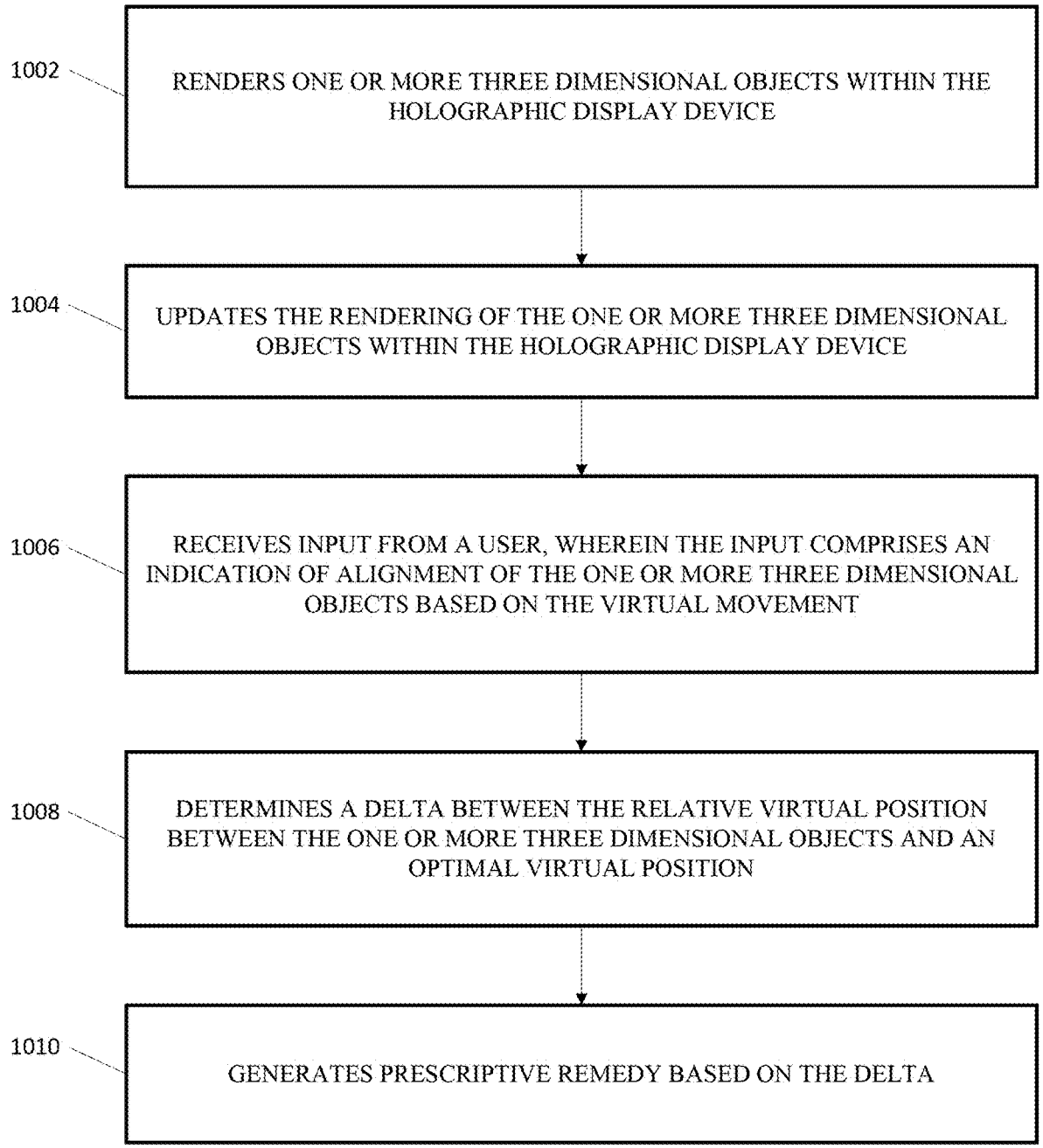
FIGS. 10A-10D are block diagrams illustrating methods for utilizing the holographic eye testing device according to an exemplary embodiment.

FIG. 10A illustrates a method for diagnosis and prescription of remedies for visual impairment in accordance with an exemplary embodiment.

At step 1002, the holographic display device renders one or more three dimensional objects with the holographic display device. The rendering corresponds to a virtual level of depth viewable by a user.

At step 1004, the holographic display device updates the rendering of the one or more three dimensional objects within the holographic display device. The updated rendering includes a virtual movement of the one or more three dimensional objects within the virtual level of depth. The virtual movement includes moving the one or more three dimensional objects laterally in the field of view of the user. Alternatively, the virtual movement includes moving the one or more three dimensional objects vertically in the field of view of the user. Additionally, the virtual movement includes moving the one or more three dimensional objects from a distal position to proximal position within the field of view of the user. The virtual level of depth corresponds to a simulated distance away from the user. The simulated distance can range from sixteen (16) inches to twenty (20) feet from the user.

At step 1006, the holographic display device receives input from a user. The input can include an indication of alignment of the one or more three dimensional objects based on the virtual movement. The indication of alignment can include a relative virtual position between the one or more three dimensional objects. The input from the user can include hand gestures and voice commands At step 1008, the holographic display device determines a delta between the relative virtual position of the one or more three dimensional objects and an optimal virtual position.

At step 1010, the holographic display device generates a prescriptive remedy based on the delta between the relative virtual position of the one or more three dimensional objects and the optimal virtual position.

Figure 10B:
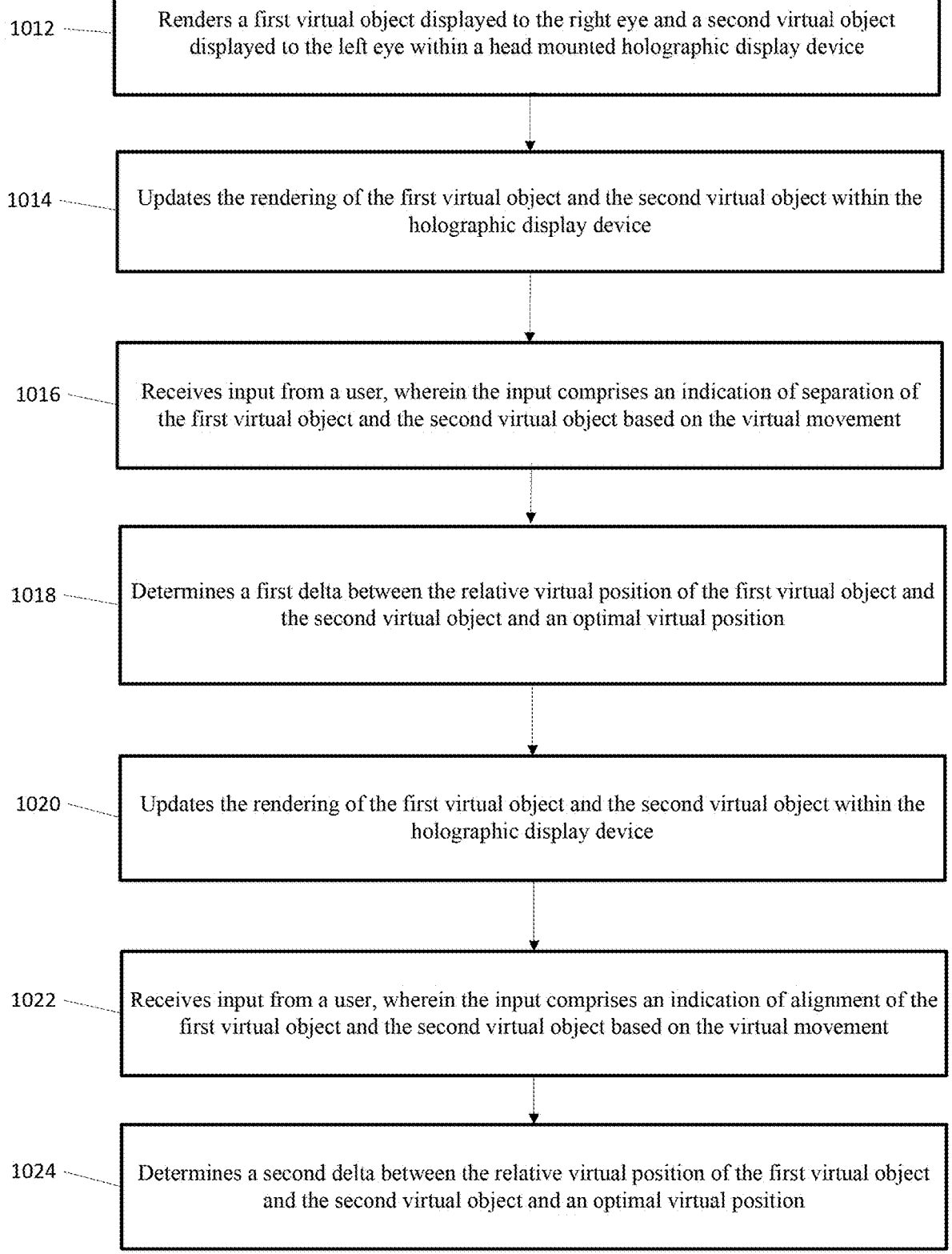

FIG. 10B illustrates a method for diagnosis and prescription of remedies for visual impairment in accordance with an exemplary embodiment.

At step 1012, a diagnostic module configured to execute on a computing device communicatively coupled to the head mounted holographic display device renders a first virtual object displayed to the right eye and a second virtual object displayed to the left eye within a head mounted holographic display device. The rendering corresponds to the first virtual object and the second virtual object aligned to appear as one virtual object to a user.

At step 1014, the diagnostic module updates the rendering of the first virtual object and the second virtual object within the holographic display device. The update includes a virtual movement of the first virtual object in a first direction and the second virtual object in a second direction opposite the first direction.

At step 1016, the diagnostic module receives input from a user. The input includes an indication of separation of the first virtual object and the second virtual object based on the virtual movement. The indication of separation comprises a relative virtual position between the first virtual object and the second virtual object where the user views the first virtual object and the second virtual object as separate objects.

At step 1018, the diagnostic module determines a first delta between the relative virtual position of the first virtual object and the second virtual object and an optimal virtual position.

At step 1020, the diagnostic module updates the rendering of the first virtual object and the second virtual object within the holographic display device. The update includes a virtual movement of the first virtual object in the second direction and the second virtual object in the first direction.

At step 1022, the diagnostic module receives a second input from the user. The input includes an indication of alignment of the first virtual object and the second virtual object based on the virtual movement. The indication of alignment comprises a relative virtual position between the first virtual object and the second virtual object where the user views the first virtual object and the second virtual object as aligned to appear as one virtual object.

At step 1024, the diagnostic module determines a second delta between the relative virtual position of the first virtual object and the second virtual object and an optimal virtual position.

Figure 10C:
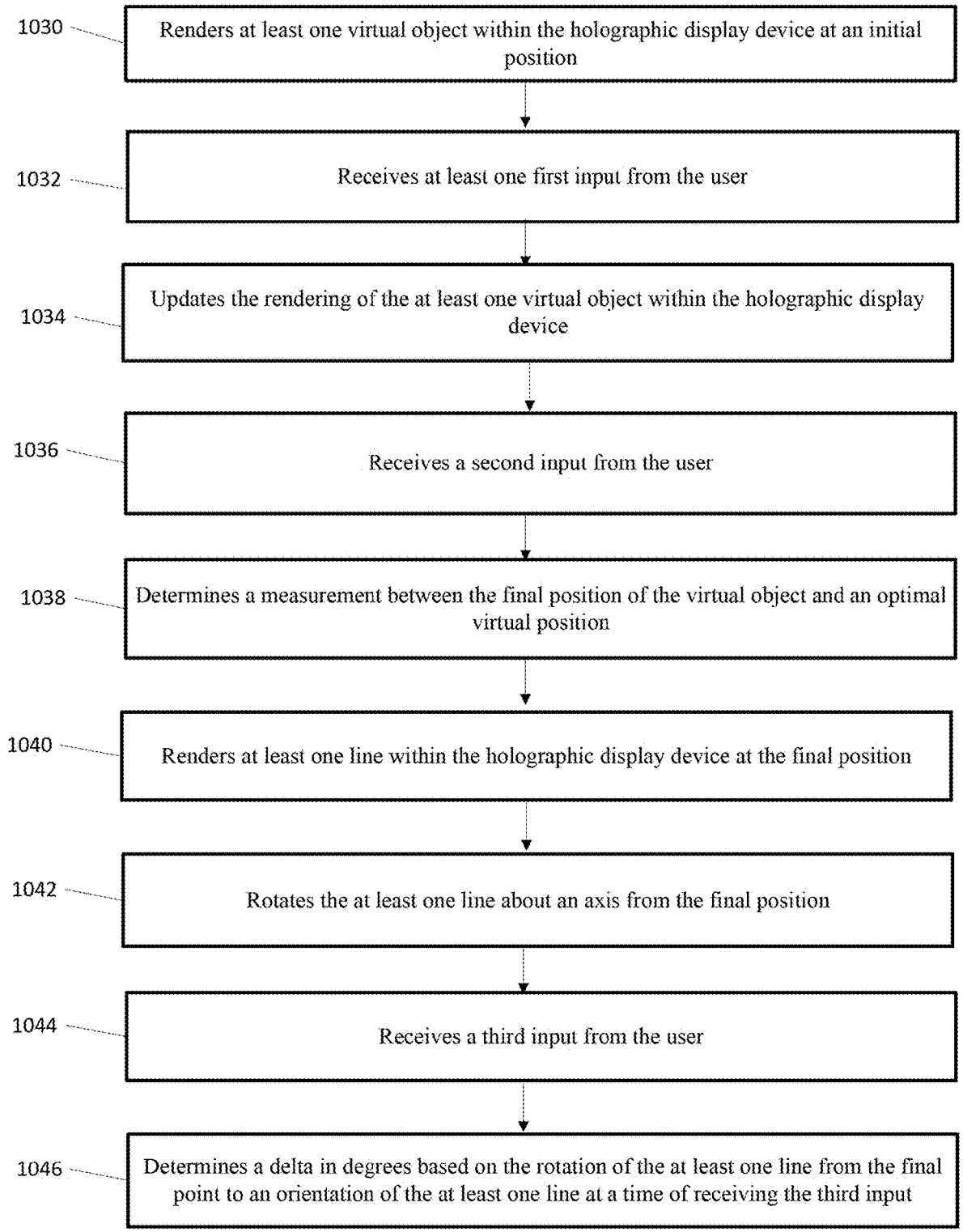

FIG. 10C illustrates a method for diagnosis and prescription of remedies for visual impairment in accordance with an exemplary embodiment.

At step 1030, the diagnostic module renders at least one virtual object within the holographic display device at an initial position. The rendering corresponds to a virtual level of depth corresponding to an initial simulated distance away from a user.

At step 1032, the diagnostic module receives at least one first input from the user. The at least one first input comprises an indication to move the at least one virtual object virtually towards or away from the user.

At step 1034, the diagnostic module updates the rendering of the at least one virtual object within the holographic display device. The update includes a virtual movement of the at least one virtual object in a direction towards or away from the user.

At step 1036, the diagnostic module receives a second input from the user. The second input includes an indication that the at least one virtual object appears clear to the user at a final position. The rendering corresponds to a virtual level of depth corresponding to a final simulated distance away from the user.

At step 1038, the diagnostic module determines a measurement between the final position of the virtual object and an optimal virtual position.

At step 1040, the diagnostic module renders at least one line within the holographic display device at the final position.

At step 1042, the diagnostic module rotates the at least one line about an axis from the final position.

At step 1044, the diagnostic module receives a third input from the user. The third input comprises an indication that the at least one line appears to the user to have rotated ninety degrees about the axis from the final position.

At step 1046, the diagnostic module determines a delta in degrees based on the rotation of the at least one line from the final point to an orientation of the at least one line at a time of receiving the third input.

Figure 10D:
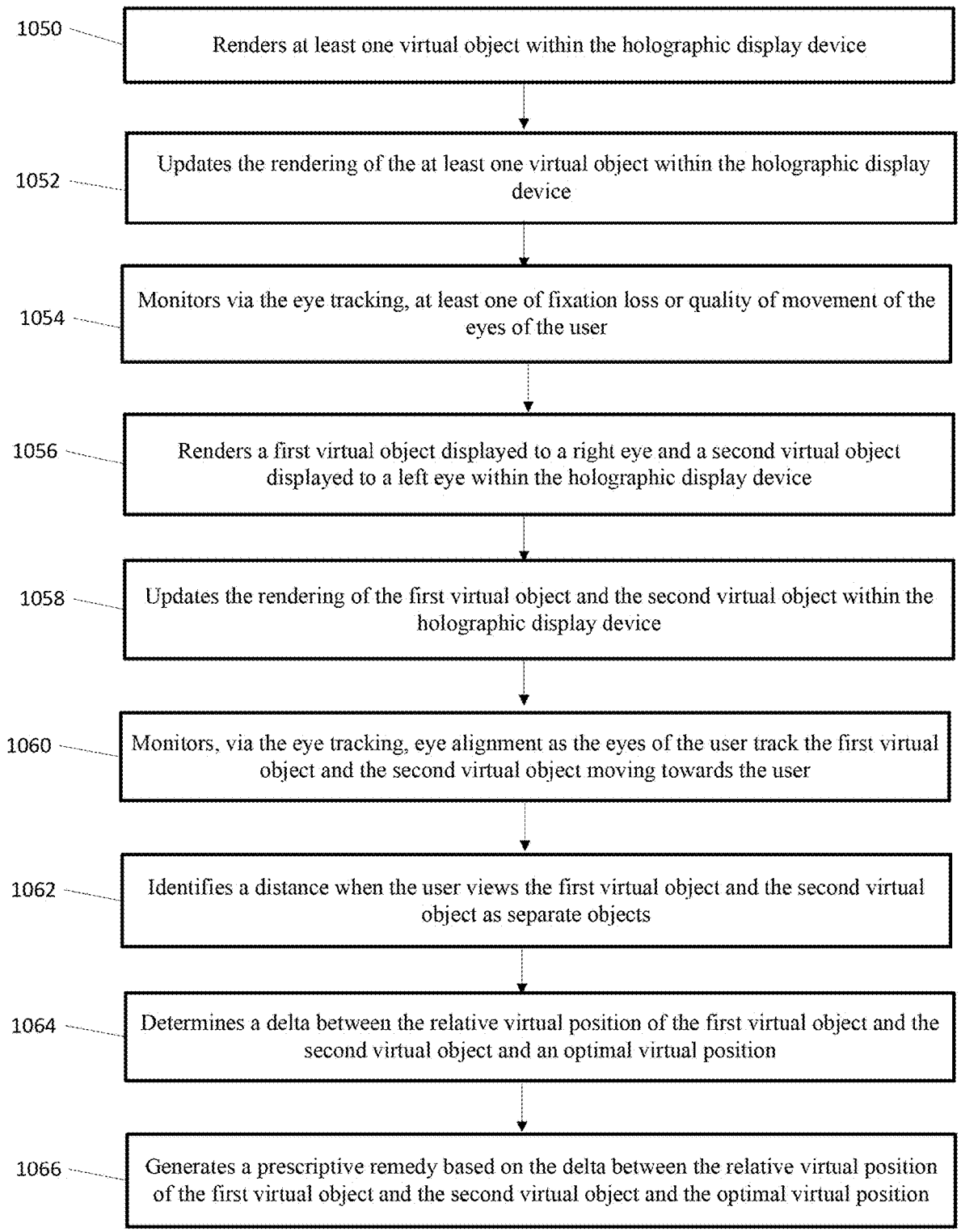

FIG. 10D illustrates a method for diagnosis and prescription of remedies for visual impairment in accordance with an exemplary embodiment.

At step 1050, the diagnostic module renders at least one virtual object within the holographic display device. The rendering corresponds to a virtual level of depth viewable by the user.

At step 1052, the diagnostic module updates the rendering of the at least one virtual object within the holographic display device. The update includes a virtual movement of the at least one virtual object within the virtual level of depth.

At step 1054, the diagnostic module monitors, via eye tracking, at least one of fixation loss or quality of movement of the eyes of the user.

At step 1056, the diagnostic module renders a first virtual object displayed to a right eye and a second virtual object displayed to a left eye within the holographic display device. The rendering corresponds to the first virtual object and the second virtual object aligned to appear as one virtual object to a user.

At step 1058, the diagnostic module updates the rendering of the first virtual object and the second virtual object within the holographic display device. The update includes a virtual movement of the first virtual object and the second virtual object towards the user.

At step 1060, the diagnostic module monitors, via the eye tracking, eye alignment as the eyes of the user track the first virtual object and the second virtual object moving towards the user.

At step 1062, the diagnostic module identifies a distance when the user views the first virtual object and the second virtual object as separate objects.

At step 1064, the diagnostic module determines a delta between the relative virtual position of the first virtual object and the second virtual object and an optimal virtual position.

At step 1066, the diagnostic module generates a prescriptive remedy based on the delta between the relative virtual position of the first virtual object and the second virtual object and the optimal virtual position.

Figure 11:
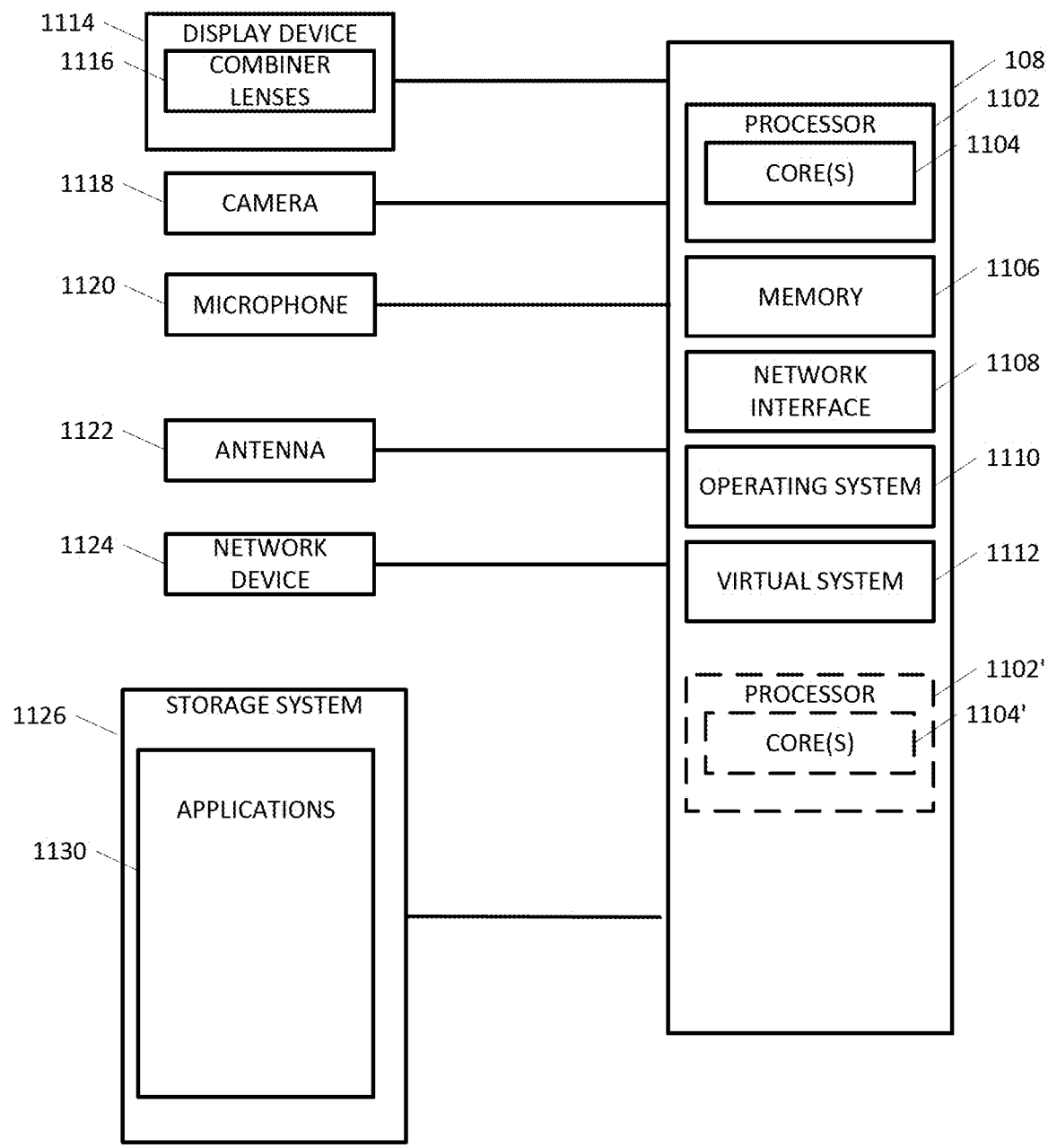
FIG. 11 depicts a block diagram an exemplary computing device in accordance with an exemplary embodiment.

FIG. 11 depicts a block diagram an exemplary computing device in accordance with an exemplary embodiment. Embodiments of the computing device 1100 can implement embodiments of the system including the holographic eye testing device. For example, the computing device can be embodied as a portion of the holographic eye testing device, and supporting computing devices. The computing device 1100 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives, one or more solid state disks), and the like. For example, memory 1106 included in the computing system 108 may store computer-readable and computer-executable instructions or software (e.g., applications 1130 such as rendering application) for implementing exemplary operations of the computing device 1100. The computing system 108 also includes configurable and/or programmable processor 1102 and associated core(s) 1104, and optionally, one or more additional configurable and/or programmable processor(s) 1102' and associated core(s) 1104' (for example, in the case of computer systems having multiple processors/cores), for executing computer-readable and computer-executable instructions or software stored in the memory 1106 and other programs for implementing exemplary embodiments of the present disclosure. Processor 1102 and processor(s) 1102' may each be a single core processor or multiple core (1104 and 1104') processor. Either or both of processor 1102 and processor(s) 1102' may be configured to execute one or more of the instructions described in connection with computing system 108.

Virtualization may be employed in the computing system 108 so that infrastructure and resources in the computing system 108 may be shared dynamically. A virtual machine 1112 may be provided to handle a process running on multiple processors so that the process appears to be using only one computing resource rather than multiple computing resources. Multiple virtual machines may also be used with one processor.

Memory 1106 may include a computer system memory or random access memory, such as DRAM, SRAM, EDO RAM, and the like. Memory 1106 may include other types of memory as well, or combinations thereof. The computing system 108 can receive data from input/output devices. A user may interact with the computing system 108 through a visual display device 1114, such as a combiner lenses 1116, which may display one or more virtual graphical user interfaces, a microphone 1120 and one or more cameras 1118.

The computing system 108 may also include one or more storage devices 1126, such as a hard-drive, CD-ROM, or other computer readable media, for storing data and computer-readable instructions and/or software that implement exemplary embodiments of the present disclosure. For example, exemplary storage device 1126 can include storing information associated with platform software and the application software.

The computing system 108 can include a network interface 1108 configured to interface via one or more network devices 1124 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing system can include one or more antennas 1122 to facilitate wireless communication (e.g., via the network interface) between the computing system 108 and a network and/or between the computing system 108 and other computing devices. The network interface 1108 may include a built-in network adapter, network interface card, PCMCIA network card, card bus network adapter, wireless network adapter, USB network adapter, modem or any other device suitable for interfacing the computing system 108 to any type of network capable of communication and performing the operations described herein.

The computing system 108 may run any operating system 1110, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing system 108 and performing the operations described herein. In exemplary embodiments, the operating system 1110 may be run in native mode or emulated mode. In an exemplary embodiment, the operating system 1110 may be run on one or more cloud machine instances.

Figure 12:
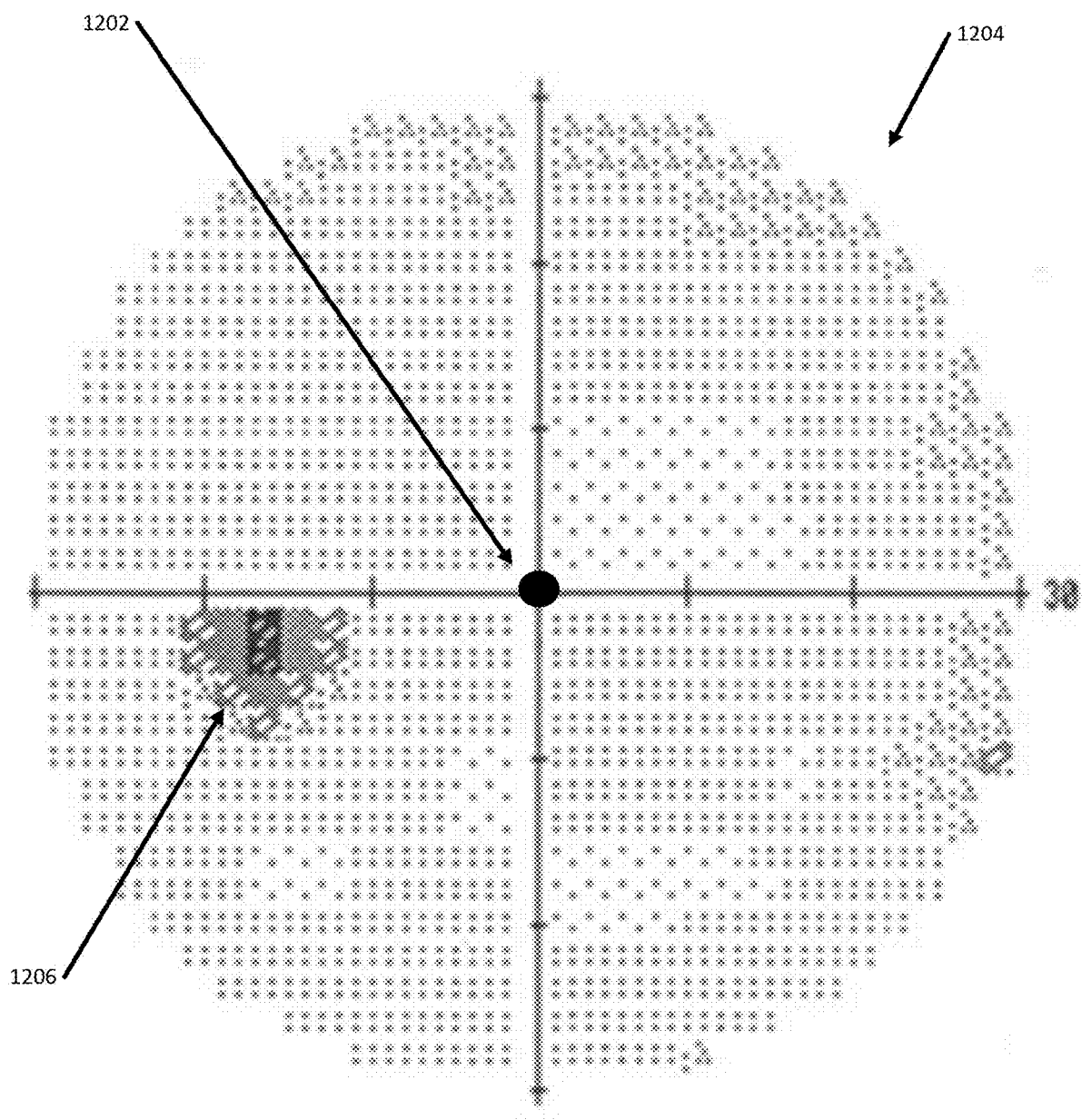
FIG. 12 illustrates a visual field test rendered in VR and/or AR via the holographic eye testing device, in accordance with an exemplary embodiment.

FIG. 12 illustrates a visual field test rendered in VR and/or AR via the holographic eye testing device, in accordance with an exemplary embodiment. The visual field test may be dynamic and/or static, as explained below. A visual field is how wide of an area an eye can see when focused on a central point. The visual field testing described herein is a method to measure how much vision there is in an eye, and how much vision loss may have occurred in the eye over time by determining how a user views objects in the user's field of vision. A visual field test can determine if there is blind spot(s) (called scotoma) in a user's vision and where the blind spot(s) are located. A scotoma's size and shape can show how eye disease or a brain disorder is affecting vision.

In an exemplary embodiment, the visual field test is administered to one eye at a time. This may be accomplished by blacking out or turning off one of the combiner lenses (e.g., combiner lenses 104A or 104B). The holographic eye testing device may include the user's lens prescription placed in front of the eye to ensure that the user is seeing as well as possible.

For the static visual field testing, the user wearing the holographic eye testing device looks at a virtual center target 1202 throughout the test. For example, the virtual center target 1202 may appear as a solid black circle. In one embodiment, small dim virtual lights begin to appear in different places throughout the user's field of vision. For example, a light may blink in different places throughout the user's field of vision. The user presses a button and/or vocally indicates whenever the user sees a light. The computing device 108 tracks which lights the user did not see (e.g. the user does not press the button or vocally indicate seeing the light).

This process assists in creating a detailed map 1204 of where the user can and cannot see. The detailed map 1204 indicates which lights the user sees outside of the user's central area of vision, such as whether there is peripheral vision loss. For example, the cluster or darken area 1206 indicates that the user did not see some or all of the lights presented in that area of the visual field.

In other embodiments, instead of presenting small, dim virtual lights, the holographic eye testing device may present virtual objects, figures, or shapes.

In some embodiments, lights are shown in some areas where the computing device 108 knows that the user cannot see them. This is done deliberately to find a visual threshold, the area where the user cannot see lights half of the time.

The dynamic visual field testing is similar to the static visual field testing described above, except that the dynamic visual field testing uses moving virtual lights instead of blinking lights.

In some embodiments, the holographic eye testing device uses an optical illusion to check for vision loss. For example, vertical bars (usually black and white) appear within the user's field of vision. These bars flickers at varying rates. If the user is not able to see the vertical bars at certain times during the test, it may indicate vision loss in certain parts of the visual field.

Figure 13:
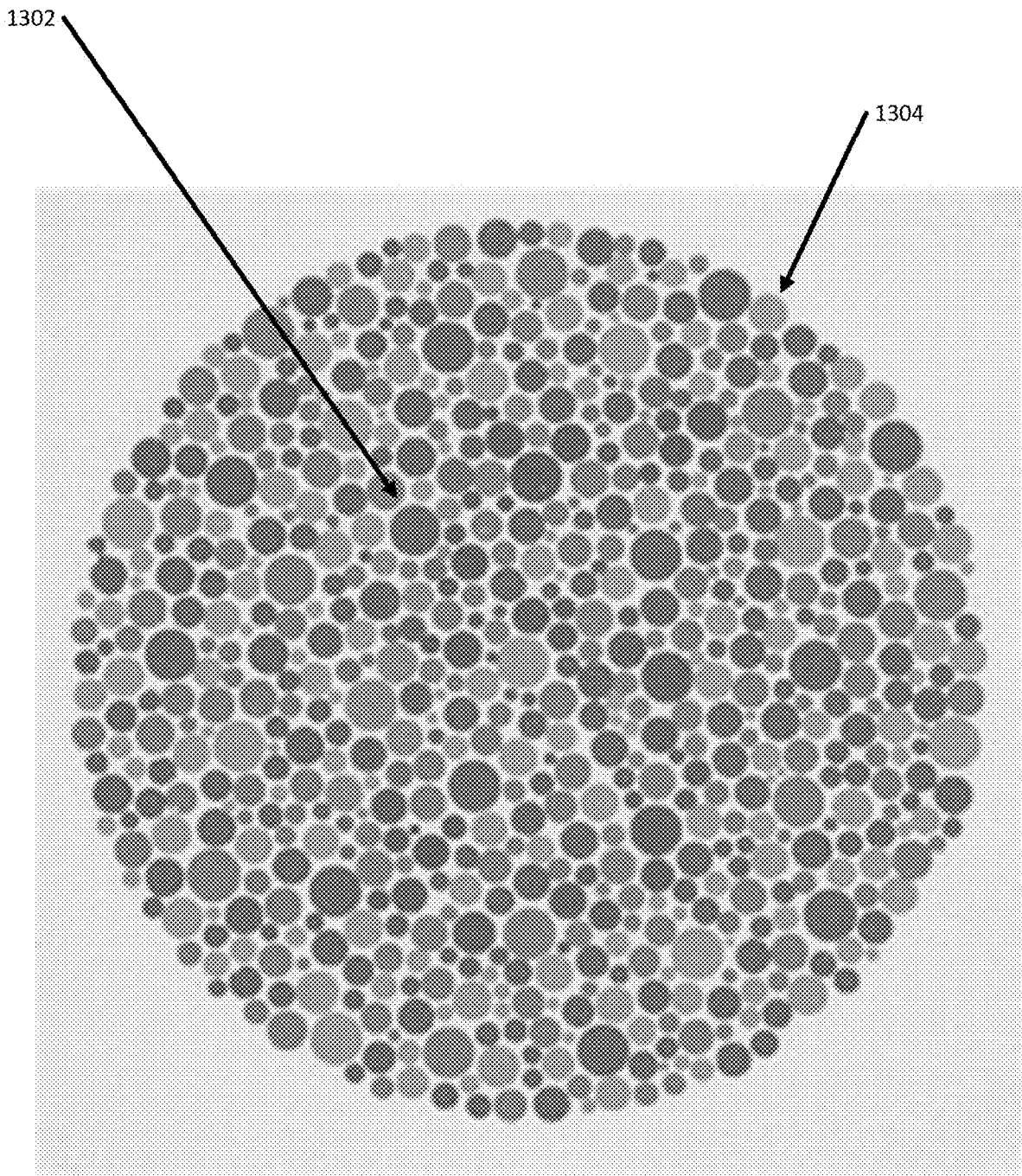
FIG. 13 illustrates color vision testing rendered in VR and/or AR via the holographic eye testing device, in accordance with an exemplary embodiment.

FIG. 13 illustrates color vision testing rendered in VR and/or AR via the holographic eye testing device, in accordance with an exemplary embodiment. The color vision testing may include Ishihara type, D-15, and other Farnsworth tests. The holographic eye testing device presents to a user a shape 1302, such as a colored number, letter, or figure, within a colored background 1304. In one embodiment, the shape 1302 and/or the background 1304 may be comprised of colored dots, as shown. The shape 1302 and the background 1304 are different colors from each other such that the shape 1302 stands out from the background 1304. In some embodiments, the colors of the shape and background are purposely pale and are carefully chosen from hues that are difficult for a color-deficient user to distinguish. Users with defective color vision see either no pattern at all or an alternative pattern based on brightness rather than hue.

In an exemplary embodiment, the color vision test is administered to one eye at a time. This may be accomplished by blacking out or turning off one of the combiner lenses (e.g., combiner lenses 104A or 104B). The holographic eye testing device may include the user's lens prescription placed in front of the eye to ensure that the user is seeing as well as possible.

In another embodiments, the holographic eye testing device presents the user with a specific number of colored virtual objects, each object including a different hue. The hues are more saturated, and they cover the spectrum so that the user will confuse colors for which they have deficient perception (such as red and green). The user is asked to virtually arrange the objects in sequence, for example, using a hand to virtually move each object or using a controller. The user virtually arranges the colors by similarity in a sequential color series. Errors can be plotted on a simple circular diagram to define the nature of the color deficiency. This arrangement may be designed for evaluation of fine hue discrimination (FM 100-hue test), for evaluation of color confusion (Farnsworth Panel D-15, Lanthony Desaturated Panel, Lanthony New Color Test), for evaluation of neutral zones or colors seen as gray (Lanthony New Color Test), and for evaluation of saturation discrimination.

Figure 14:
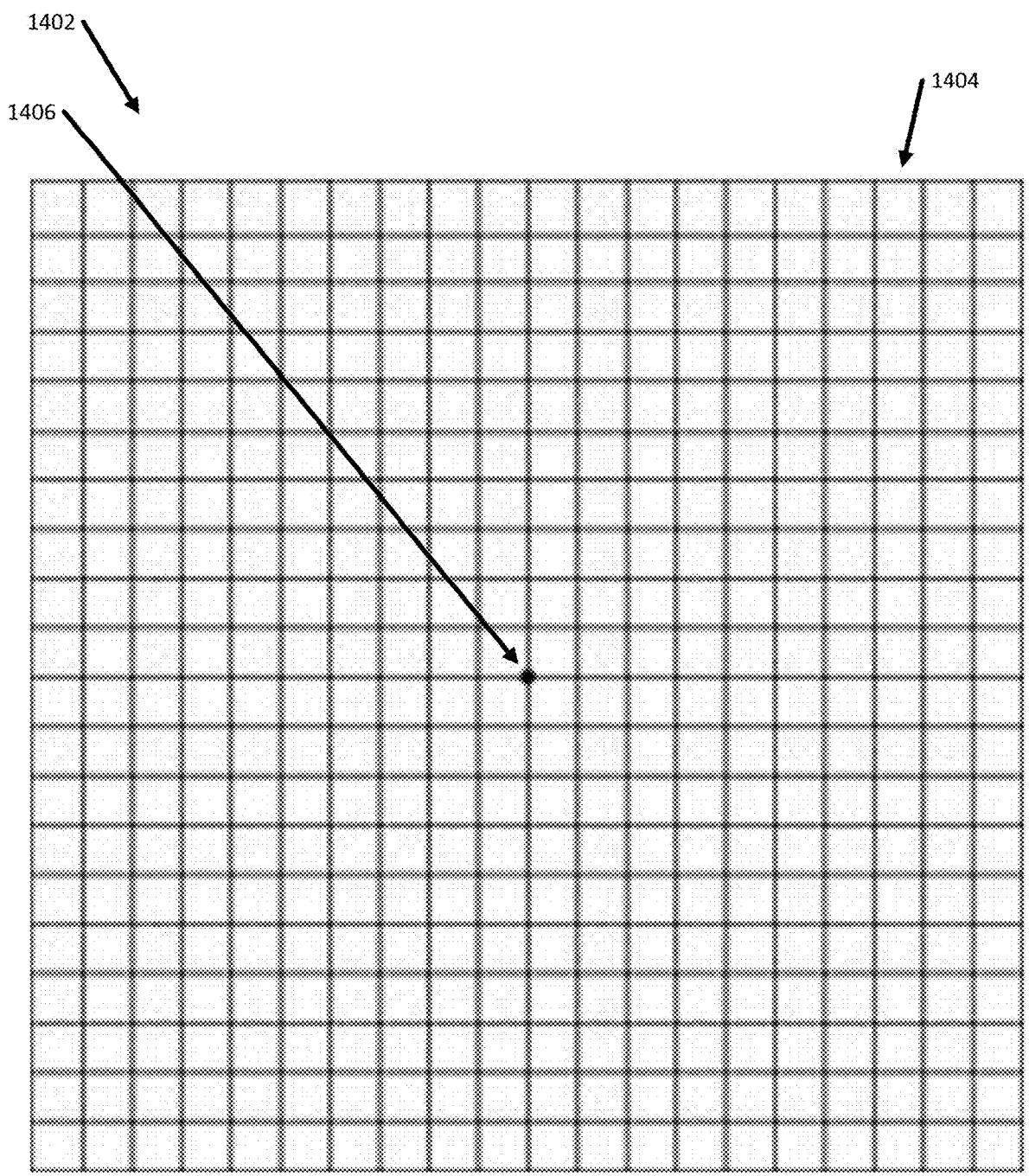
FIG. 14 illustrates an Amsler grid visual field test rendered in VR and/or AR via the holographic eye testing device, in accordance with an exemplary embodiment.

FIG. 14 illustrates an Amsler grid visual field test rendered in VR and/or AR via the holographic eye testing device, in accordance with an exemplary embodiment. The Amsler grid visual field test is used to detect potential field loss or distortions caused by retinal detachments and macula pathology. The holographic eye testing device displays a virtual pattern of straight lines that makes a grid 1402 of many equal squares 1404 and a virtual center focal point 1406 or focal target. In an exemplary embodiments, the center focal point 1406 is a black dot. For example, the grid may include 0.5 centimeters (cm) squares that form a larger square of 10 cm by 10 cm. This test evaluates 10 degrees of vision from a focal point which overall evaluates a visual acuity of 20 degrees. The user looks at a dot in the middle of the grid and describe any areas that may appear wavy, blurry or blank.

In an exemplary embodiment, the Amsler grid visual field test is administered to one eye at a time. This may be accomplished by blacking out or turning off one of the combiner lenses (e.g., combiner lenses 104A or 104B). The holographic eye testing device may include the user's lens prescription placed in front of the eye to ensure that the user is seeing as well as possible.

In some embodiments, the grid 1402 further includes four diagonal lines to assist the user to focus on the center dot, for example if the user has a central scotoma (blind spot in the middle of the visual field).

In some embodiments, the grid 1402 further includes different color lines, background, and/or dot, such as a black background with red lines and a red dot. This grid is helpful in identifying disorders that have an associated red desaturation such as pituitary tumor causing partial blindness, toxic maculopathy, or toxic optic neuropathy.

In some embodiments, the grid 1402 further includes a black background with a large central white dot with randomly placed smaller dots throughout the grid. There may be no lines in this grid. This grid may be used to differentiate between blind spots and distortions.

In some embodiments, the grid 1402 further includes a black background with white horizontal lines with a white dot in the center. The horizontal lines may help determine distortions related to curved sections of the cornea.

In some embodiments, the grid 1402 further includes a white background and black lines. Towards the black dot in the center, the horizontal lines are closer than the horizontal lines further from the black dot. This can be helpful in identifying fine visual distortions near the center of your visual field.

In some embodiments, the grid 1402 further includes another smaller grid at the center around the central dot. This allows identification of disease in half a degree. This is helpful in identification of macular degeneration.

During the Amsler grid visual field test, the user focuses on the center focal point 1406 and identifies, either verbally or using a controller, whether the dot in the center is visible, whether the user can see the four corners and the four sides of the grid while focusing on the dot in the center, whether there are blank or blurry sections of the grid while focusing on the center, whether there are wavy lines (horizontal or vertical) of the grid while focusing on the center, whether there are moving lines, shiny sections and/or vibrations noted in the grid while focusing on the center. If the lines appear distorted or disappear, the user may mark the areas where these were noted. The marks may be made verbally (for example, by noting the number of squares between the dot and the abnormality), using a controller, or virtually using a hand.

The computing device 108 may store the results in the database for later reference, as changes in the area of distortion can represent a progressive condition, stabilized condition, or improvement in the user's condition.

Figure 15:
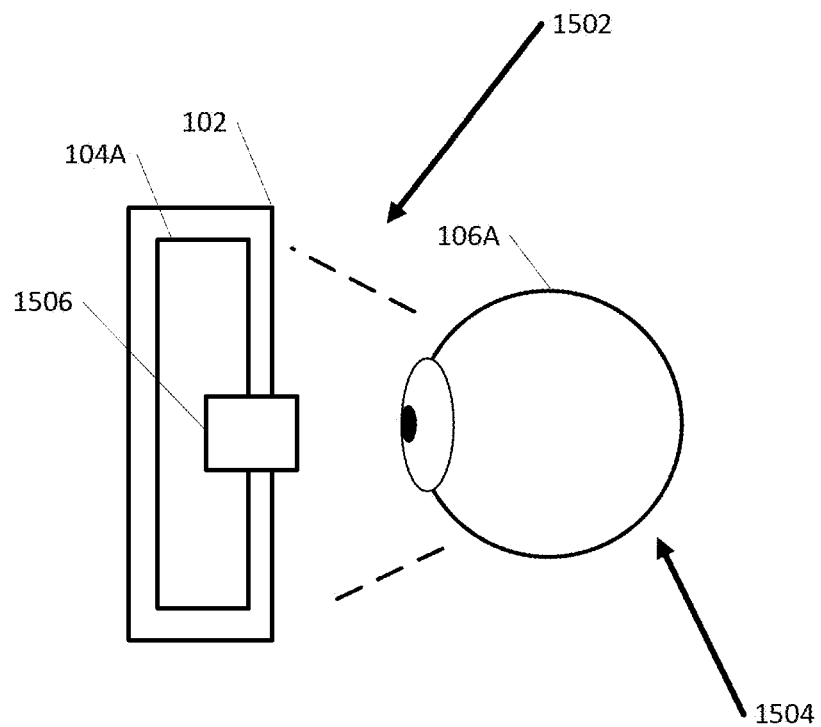
FIG. 15 illustrates a pupillometry test rendered in VR and/or AR via the holographic eye testing device, in accordance with an exemplary embodiment.

FIG. 15 illustrates a pupillometry test rendered in VR and/or AR via the holographic eye testing device, in accordance with an exemplary embodiment. Pupillometry measures the spontaneous variation of the pupil diameter and the pupillary light reflex. The holographic eye testing device shines a light 1502 in the user's eyes 1504 and measures the speed of pupillary response. The light 1502 may be a white light presented in the holographic eye testing device. For example, the holographic eye testing device may present a beam of light to a pupil and observe the size of the pupil and reaction in the eye that is lit. In another embodiment, a physical light (e.g., a flashlight, a LED light, a UV light, an incandescent light, etc.) is added to the holographic eye testing device to shine a light 1502 in the user's eyes 1504.

One or more cameras 1506 are coupled to the holographic eye testing device and obtain images (e.g., pictures and video) of the pupil before, during, and/or after the light 1502 is presented to the user's eye. The computing device 108 uses the images to determine the sizes of the pupil before, during, and/or after the light 1502 is presented to the user's eye. The pupillometry test is used to detect neurological disorders such as Parkinson's or Alzheimer's and a test for concussions.

The computing device 108 may store the results in the database for later reference, as changes in the sizes of the pupil can represent a progressive condition, stabilized condition, or improvement in the user's condition.

Figure 16:
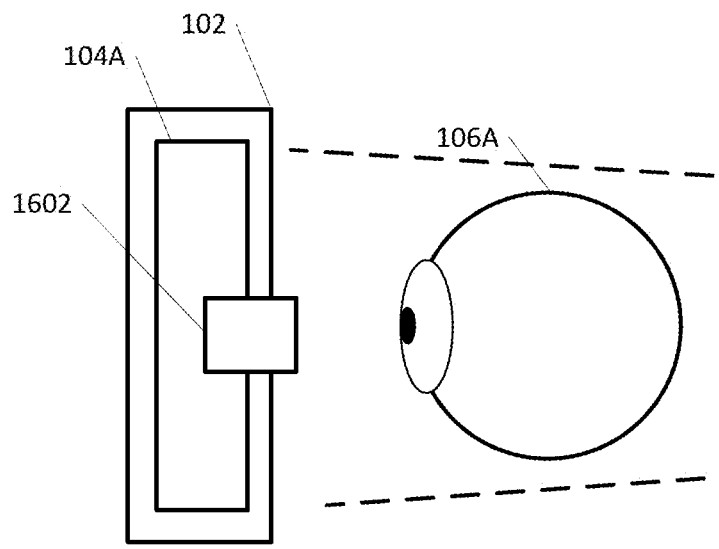
FIG. 16 illustrates a retinal scan test rendered in VR and/or AR via the holographic eye testing device, in accordance with an exemplary embodiment.

FIG. 16 illustrates a retinal scan test rendered in VR and/or AR via the holographic eye testing device, in accordance with an exemplary embodiment. An iris biometrics module 1602 can be integrated into the holographic eye testing device and/or computing device 108 to capture the user's iris and do eye-tracking at the same time. The iris biometrics module 1602 uses retinal scans to map the unique patterns of the user's retina. The retinal scan is performed by casting an unperceived beam of low-energy infrared light emitted by the holographic eye testing device into a person's eye as they look within or through the holographic eye testing device. This beam of light traces a standardized path on the retina. Once the iris biometrics module 1602 captures a retinal image, specialized software in the iris biometrics module 1602 compiles the unique features of the network of retinal blood vessels into a template. The iris biometrics module 1602 may further identify cataract and/or foreign bodies.

Figure 17:
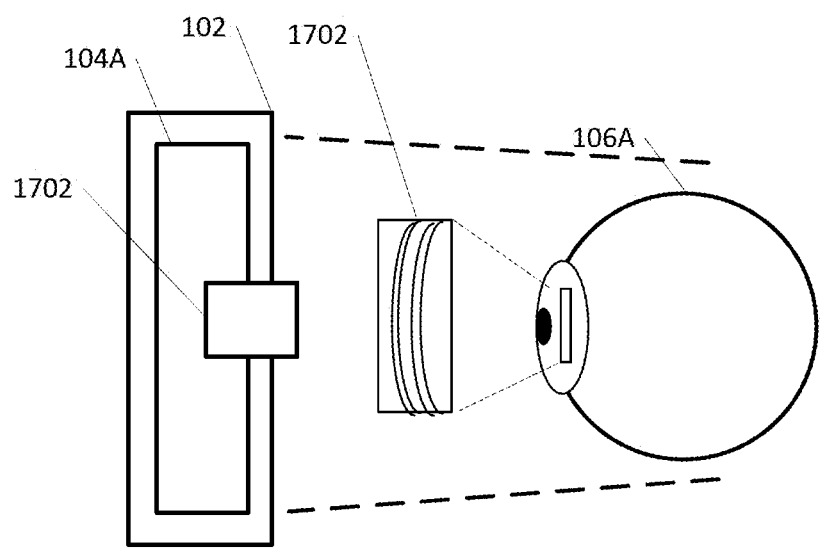
FIG. 17 illustrates a tear breakup time test via the holographic eye testing device, in accordance with an exemplary embodiment.

FIG. 17 illustrates a tear breakup time test via the holographic eye testing device, in accordance with an exemplary embodiment. Tear breakup time (TBUT) is a clinical test used to assess for evaporative dry eye disease. An eye analysis module 1702 is integrated into the holographic eye testing device to capture images of the tear film 1702 which upon specialized software in the eye analysis module 1702 performs analysis to identify dry spots. To measure TBUT, fluorescein is instilled into the user's tear film 1702 before the user places his or her head into the holographic eye testing device. The user is asked not to blink while the tear film 1702 is observed under a broad beam of cobalt blue illumination emitted by the holographic eye testing device. The holographic eye testing device records the TBUT as the number of seconds that elapse between the last blink and the appearance of the first dry spot in the tear film, as seen in this progression of the images captured by the eye analysis module 1702 over time.

Figure 18:
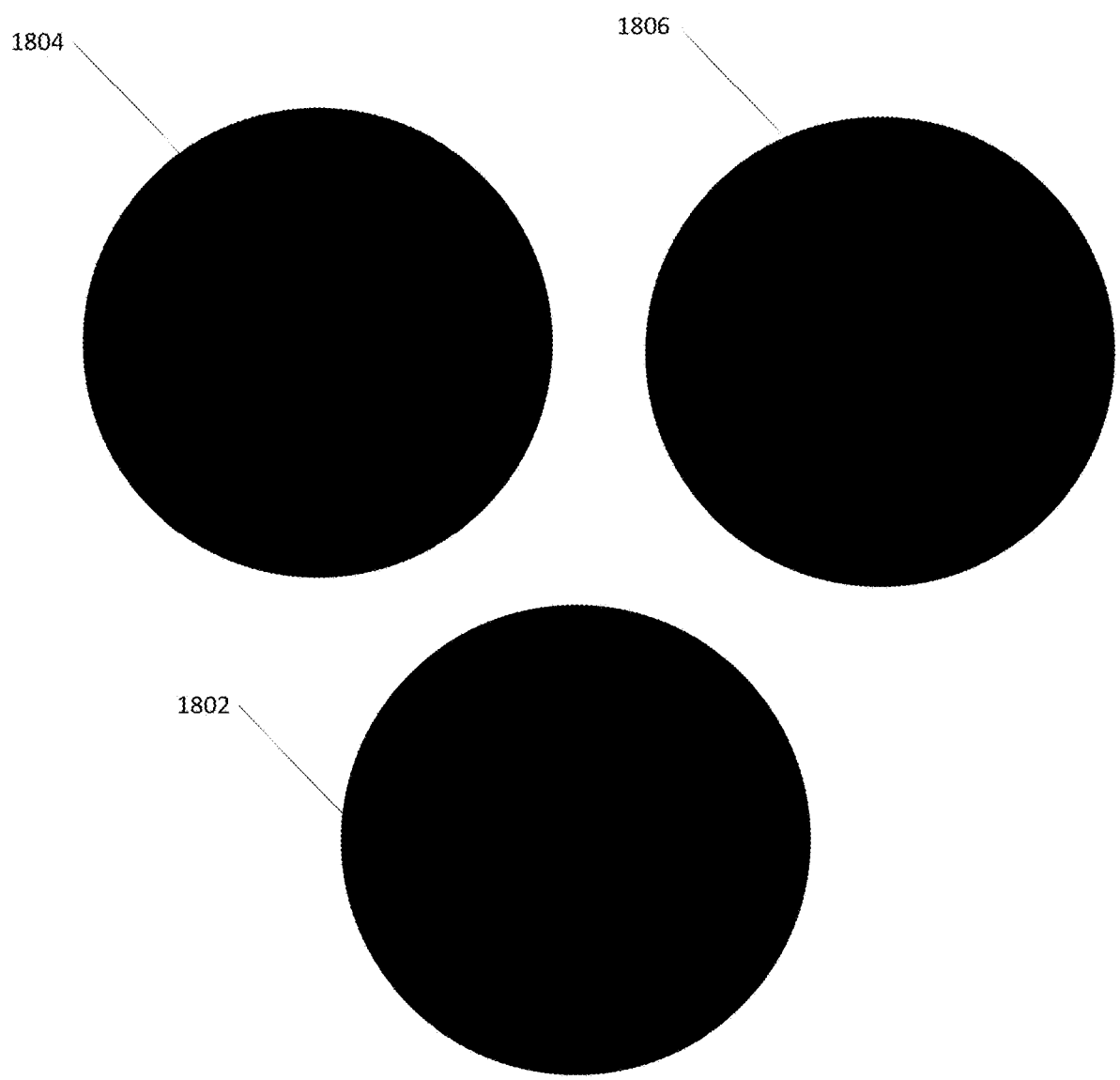
FIG. 18 illustrates a syntonics color therapy test via the holographic eye testing device, in accordance with an exemplary embodiment.

FIG. 18 illustrates a syntonics color therapy test via the holographic eye testing device, in accordance with an exemplary embodiment. Syntonics is a form of light therapy used to treat vision problems. For example, a patient whose eyes turn in would most likely view a different color than a patient whose eyes turn out. The holographic eye testing device displays a variety of colors 1802, 1804, 1806 on the spectrum to the user based on the user's vision problem. While three colors are illustrated in the figure, more or less colors may be used without departing from this embodiment. The colors may be displayed as shapes or blotches. During the test, the user verbally identifies each color 1802, 1804, 1806 displayed by the holographic eye testing device. The identified color is recorded by the holographic eye testing device and saved in a database or recorded by a technician.

In some embodiments, prior to the syntonics color therapy test, multiple vision tests are performed to determine the most successful syntonic treatment. These tests include pupil reaction tests and functional vision field tests. Based on the findings of these tests, specific colors are shown to the patient based on his or her visual condition. For example, red and orange is often used to treat lazy eyes, and green or yellow is used to treat eyes that are turned inward. The blue spectrum can help improve a patient's focus while reading or doing near work.

Figure 19:
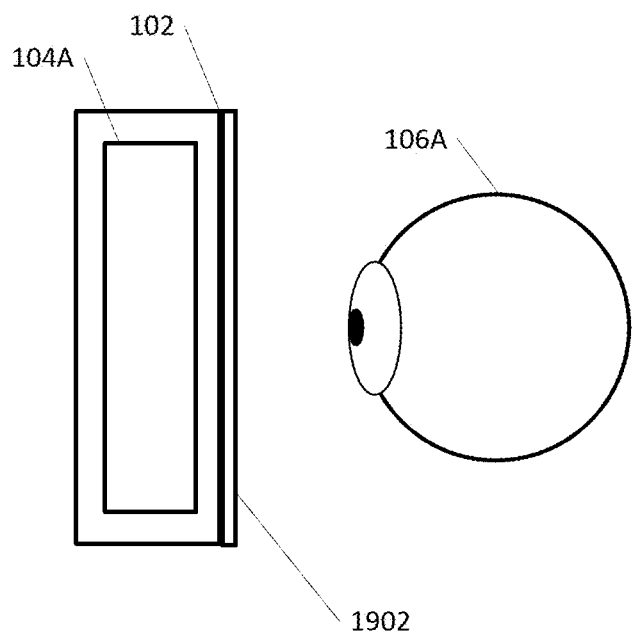
FIG. 19 illustrates a colorimetry test via the holographic eye testing device, in accordance with an exemplary embodiment.

FIG. 19 illustrates a colorimetry test via the holographic eye testing device, in accordance with an exemplary embodiment. The colorimetry test is used to sequentially explore color space to find the optimal precision tint for the relief of perceptual distortions, commonly known as visual stress. The holographic eye testing device displays a variety of tinted colors overlaid on text to the user. The holographic eye testing device may display one tinted color at a time or two or more rows of different tinted colors. Assessment involves the presentation of each overlay in turn for comparison with others shown previously or placed beside it.

In one embodiment, a physical tint 1902 of a specified tinted color, such as a tinted transparent plastic material, is placed between the user's eye and the combiner lenses (e.g., combiner lenses 104A or 104B). In another embodiment, the tint is virtually produced over the text as the user views the text within the holographic eye testing device.

Figure 20A:
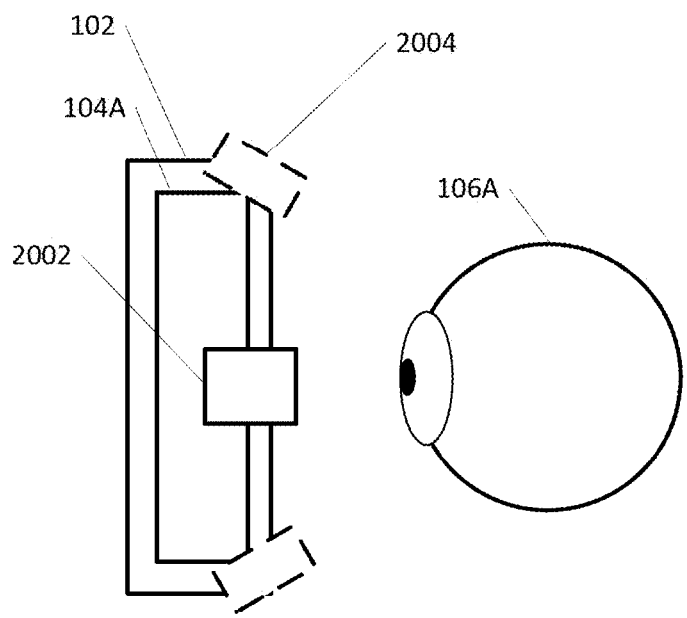
FIGS. 20A and B illustrate a keratometry test via the holographic eye testing device, in accordance with an exemplary embodiment.
Figure 20B:
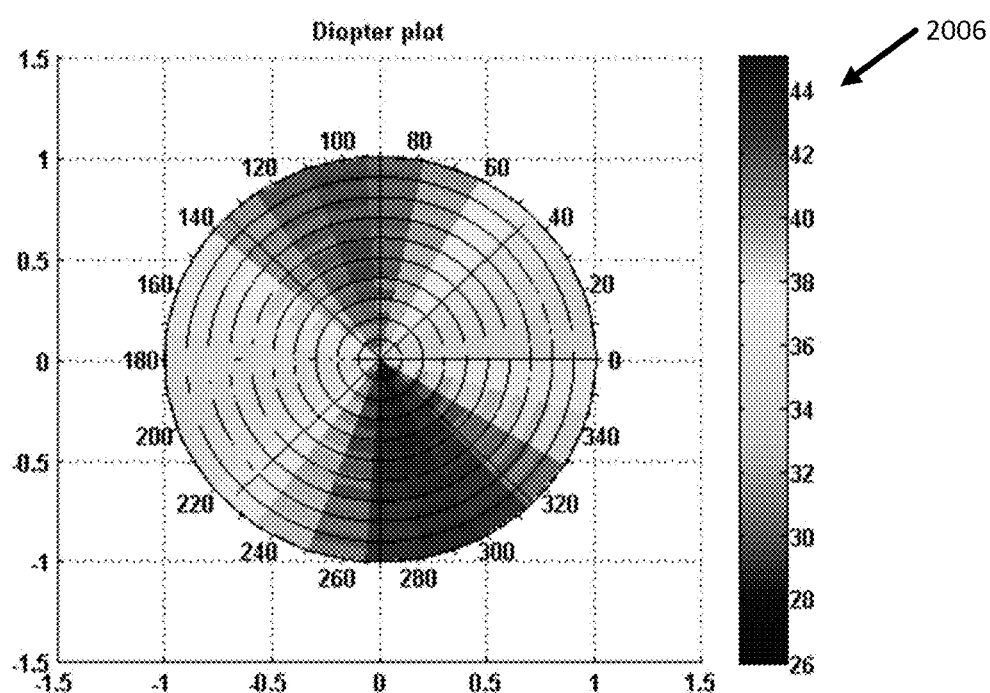

FIGS. 20A and B illustrate a keratometry test via the holographic eye testing device, in accordance with an exemplary embodiment. Keratometry is a procedure used to measure the curvature of the cornea (corneal curvature). A digital camera 2002 is integrated into the holographic eye testing device. An eye analysis module further is integrated into the holographic eye testing device and/or the computing device 108 to perform analysis as described below. The holographic eye testing device displays a virtual bowl containing an illuminated pattern, such as a series of concentric rings. Light is focused on the anterior surface of the user's cornea using light emitted from the holographic eye testing device or physical lights 2004 added to the holographic eye testing device. The light is reflected back to the digital camera 2002 at the holographic eye testing device. The topology of the cornea is revealed by the shape taken by the reflected pattern. The eye analysis module provides the necessary analysis, typically determining the position and height of several thousand points across the cornea. The eye analysis module may generate a topographical map 2006 as shown in FIG. 20B, such as sagittal map, which color-codes the steepness of curvature according to its dioptric value.

Figure 21:
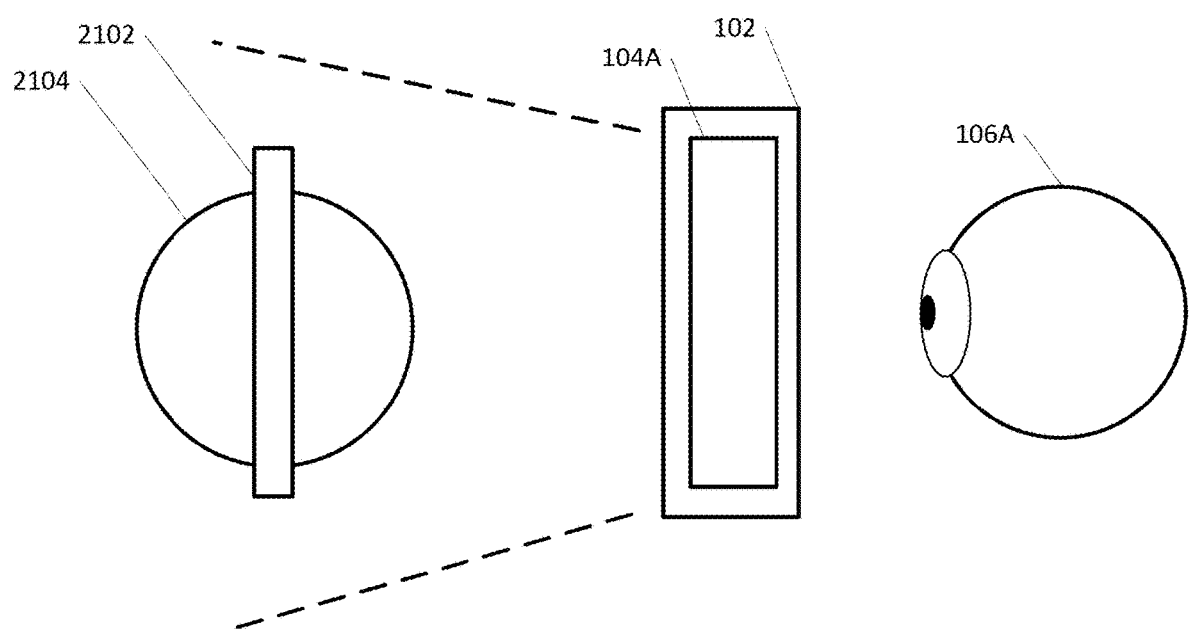
FIG. 21 illustrates depth perception eye test rendered in VR and/or AR via the holographic eye testing device, in accordance with an exemplary embodiment.

FIG. 21 illustrates depth perception eye test rendered in VR and/or AR via the holographic eye testing device, in accordance with an exemplary embodiment. The holographic eye testing device renders a virtual object 2102 in front of a virtual circle 2104. The user focuses his or her gaze primarily on the circle 2104 and typically sees two images of the object 2102 on either side of the circle 2104. The user verbally identifies or uses a controller to identify whether he or she views two objects. If the user views the two objects, it's a sign of strong depth perception.

The user may further identify whether the user views the object 2102 as larger on one side than on the other, views the object 2102 better on one side, or views only one reflection of you're the object 2102, not two. It may signal poor depth perception if any of these occur during the test.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes multiple system elements, device components, or method steps, those elements, components, or steps can be replaced with a single element, component, or step. Likewise, a single element, component, or step can be replaced with multiple elements, components, or steps that serve the same purpose. Moreover, while exemplary embodiments have been shown and described with references to particular embodiments thereof, those of ordinary skill in the art will understand that various substitutions and alterations in form and detail can be made therein without departing from the scope of the present disclosure. Further, still, other aspects, functions, and advantages are also within the scope of the present disclosure.

Exemplary flowcharts are provided herein for illustrative purposes and are non-limiting examples of methods. One of ordinary skill in the art will recognize that exemplary methods can include more or fewer steps than those illustrated in the exemplary flowcharts and that the steps in the exemplary flowcharts can be performed in a different order than the order shown in the illustrative flowcharts.

We claim:

1. A method for testing for visual impairment, comprising:
   rendering, via a computing device communicatively coupled to a head mounted holographic display device, a virtual target displayed to a user within the holographic display device;
   rendering, via the computing device, at least one virtual light within a field of vision of the user within the holographic display device;
   identifying, via the computing device, whether input was received from the user, wherein the input comprises an indication that the user identified the at least one virtual light; and
   generating, via the computing device, a map identifying one or more locations that the user identified the at least one virtual light or did not identify the at least one virtual light.

2. The method of claim 1, wherein the at least one virtual light is a small dim blinking light.

3. The method of claim 1, wherein the at least one virtual light is a small dim moving light.

4. A method for testing for visual impairment, comprising:
   rendering, via a computing device communicatively coupled to a head mounted holographic display device, a virtual pattern of straight lines that creates a grid displayed to a user within the holographic display device;

rendering, via the computing device, a virtual target within a center of the grid; and receiving, via the computing device, input from the user, wherein the input comprises an indication whether the user views at least one of the virtual target, four corners of the grid, four sides of the grid, a blank section of the grid, a blurry section of the grid, a wavy line of the grid, a moving line of the grid, a shiny section of the grid, vibrations in the grid, or disappearing lines in the grid.

5. The method of claim 4, wherein the virtual target is a center dot.

\* \* \* \* \*